(12) United States Patent
Gaustad et al.

(10) Patent No.: US 9,416,390 B2
(45) Date of Patent: Aug. 16, 2016

(54) ELECTRIC MEASUREMENT OF MONOLAYERS FOLLOWING PRO-CLEAVE DETECTION OF PRESENCE AND ACTIVITY OF ENZYMES AND OTHER TARGET ANALYTES

(71) Applicant: OHMX CORPORATION, Evanston, IL (US)

(72) Inventors: Adam G. Gaustad, Chicago, IL (US); Michael J. Ahrens, Evanston, IL (US); Paul A. Bertin, Chicago, IL (US)

(73) Assignee: OHMX Corporation, Evanston, IL (US)

( * ) Notice: Subject to any disclaimer, the term of this patent is extended or adjusted under 35 U.S.C. 154(b) by 147 days.

(21) Appl. No.: 13/952,345

(22) Filed: Jul. 26, 2013

(65) Prior Publication Data

US 2014/0027310 A1     Jan. 30, 2014

Related U.S. Application Data

(60) Provisional application No. 61/676,641, filed on Jul. 27, 2012, provisional application No. 61/677,593, filed on Jul. 31, 2012, provisional application No. 61/708,301, filed on Oct. 1, 2012.

(51) Int. Cl.
    *G01N 33/543* (2006.01)
    *C12Q 1/00* (2006.01)
    *C12Q 1/37* (2006.01)

(52) U.S. Cl.
    CPC ........ *C12Q 1/005* (2013.01); *C12Q 1/37* (2013.01); *G01N 33/5438* (2013.01); *G01N 2610/00* (2013.01)

(58) Field of Classification Search
    CPC ....... C12Q 1/005; C12Q 1/37; G01N 33/5438
    See application file for complete search history.

(56) References Cited

U.S. PATENT DOCUMENTS

| | | | |
|---|---|---|---|
| 4,247,533 | A | 1/1981 | Cerami et al. |
| 4,304,853 | A | 12/1981 | Jozefonvicz et al. |
| 4,727,036 | A | 2/1988 | Knowles et al. |
| 4,806,468 | A | 2/1989 | Wagner et al. |
| 5,206,144 | A | 4/1993 | Zeuthen et al. |

(Continued)

FOREIGN PATENT DOCUMENTS

| | | |
|---|---|---|
| EP | 02075339 | 7/2009 |
| WO | 90/01559 | 2/1990 |

(Continued)

OTHER PUBLICATIONS

International Search Report and Written Opinion dated Jan. 7, 2014 for Application No. PCT/US2013/052340.

(Continued)

*Primary Examiner* — Melanie Y Brown
(74) *Attorney, Agent, or Firm* — Wolf, Greenfield & Sacks, P.C.

(57) ABSTRACT

This invention describes methods for detecting target analytes by utilizing an electroactive moiety (EAM) that functions as a substrate for a specific enzyme. If target analyte is present, a functional group is enzymatically removed from a transition metal complex resulting in quantifiable electrochemical signal at two unique potentials, $E^0_1$ and $E^0_2$ that is detected through a self-assembled monolayer (SAM) on an electrode.

19 Claims, 12 Drawing Sheets

(56) References Cited

U.S. PATENT DOCUMENTS

| | | | |
|---|---|---|---|
| 5,270,163 A | 12/1993 | Gold et al. | |
| 5,407,759 A | 4/1995 | Ohsuga | |
| 5,475,096 A | 12/1995 | Gold et al. | |
| 5,567,588 A | 10/1996 | Gold et al. | |
| 5,595,877 A | 1/1997 | Gold et al. | |
| 5,620,850 A | 4/1997 | Bamdad et al. | |
| 5,637,459 A | 6/1997 | Burke et al. | |
| 5,654,159 A | 8/1997 | Allard et al. | |
| 5,683,867 A | 11/1997 | Biesecker et al. | |
| 5,705,337 A | 1/1998 | Gold et al. | |
| 5,834,224 A | 11/1998 | Ruger et al. | |
| 6,013,170 A * | 1/2000 | Meade | B82Y 5/00 204/403.01 |
| 6,013,459 A | 1/2000 | Meade | |
| 6,162,645 A | 12/2000 | Lee et al. | |
| 6,248,229 B1 | 6/2001 | Meade | |
| 6,348,319 B1 | 2/2002 | Braach-Maksvytis et al. | |
| 6,432,723 B1 | 8/2002 | Plaxco et al. | |
| 6,495,336 B1 | 12/2002 | Ludin et al. | |
| 6,600,026 B1 | 7/2003 | Yu | |
| 6,740,518 B1 | 5/2004 | Duong et al. | |
| 6,770,190 B1 | 8/2004 | Milanovski et al. | |
| 6,927,039 B2 | 8/2005 | Gilardi et al. | |
| 6,942,771 B1 | 9/2005 | Kayyem | |
| 6,991,926 B2 | 1/2006 | Schmid et al. | |
| 7,018,523 B2 | 3/2006 | Meade | |
| 7,160,678 B1 | 1/2007 | Kayyem et al. | |
| 7,223,837 B2 | 5/2007 | De Groot et al. | |
| 7,267,939 B2 | 9/2007 | Meade | |
| 7,312,087 B2 | 12/2007 | Duong et al. | |
| 7,393,645 B2 | 7/2008 | Kayyem et al. | |
| 7,514,228 B2 | 4/2009 | Meade | |
| 7,560,237 B2 | 7/2009 | O'Connor et al. | |
| 7,566,534 B2 | 7/2009 | Meade | |
| 7,579,145 B2 | 8/2009 | Meade | |
| 7,582,419 B2 | 9/2009 | Meade | |
| 7,595,153 B2 | 9/2009 | Meade | |
| 7,601,507 B2 | 10/2009 | O'Connor et al. | |
| 7,705,045 B2 | 4/2010 | De Groot et al. | |
| 7,713,711 B2 | 5/2010 | O'Connor et al. | |
| 7,732,140 B2 | 6/2010 | Vandenbark et al. | |
| 7,759,073 B2 | 7/2010 | O'Connor et al. | |
| 7,759,114 B2 | 7/2010 | Martin et al. | |
| 7,803,572 B2 | 9/2010 | Braven et al. | |
| 7,807,835 B2 | 10/2010 | Xie et al. | |
| 8,114,661 B2 | 2/2012 | O'Connor et al. | |
| 8,530,170 B2 | 9/2013 | Bertin | |
| 8,734,631 B2 | 5/2014 | Ahrens et al. | |
| 8,802,390 B2 | 8/2014 | Bertin et al. | |
| 8,951,400 B2 | 2/2015 | Ahrens et al. | |
| 9,194,836 B2 | 11/2015 | Bertin | |
| 2002/0058329 A1 | 5/2002 | Singh et al. | |
| 2002/0086443 A1* | 7/2002 | Bamdad | B82Y 30/00 436/526 |
| 2002/0121314 A1 | 9/2002 | Tao et al. | |
| 2002/0142411 A1 | 10/2002 | Hainfeld | |
| 2003/0073243 A1 | 4/2003 | Law et al. | |
| 2003/0119208 A1 | 6/2003 | Yoon et al. | |
| 2004/0018611 A1* | 1/2004 | Ward | B82Y 15/00 435/287.2 |
| 2004/0023258 A1* | 2/2004 | Patolsky et al. | 435/6 |
| 2005/0123948 A1 | 6/2005 | Claycomb et al. | |
| 2005/0148101 A1 | 7/2005 | Bamdad et al. | |
| 2005/0189240 A1 | 9/2005 | Lin et al. | |
| 2006/0003382 A1* | 1/2006 | Eckermann et al. | 435/7.1 |
| 2006/0134713 A1* | 6/2006 | Rylatt et al. | 435/7.92 |
| 2007/0111224 A1 | 5/2007 | Jung et al. | |
| 2008/0081329 A1* | 4/2008 | Elliott | C12Q 1/6825 435/6.11 |
| 2008/0164154 A1 | 7/2008 | Purvis | |
| 2008/0248592 A1 | 10/2008 | Bamdad et al. | |
| 2009/0041791 A1 | 2/2009 | Feng | |
| 2009/0061451 A1* | 3/2009 | Achim et al. | 435/6 |
| 2009/0099434 A1* | 4/2009 | Liu et al. | 600/347 |
| 2009/0107852 A1* | 4/2009 | Labgold | C12Q 1/6825 205/777.5 |
| 2009/0253149 A1 | 10/2009 | Ahrens et al. | |
| 2010/0003710 A1* | 1/2010 | Bertin et al. | 435/24 |
| 2010/0025264 A1 | 2/2010 | Yuan et al. | |
| 2010/0145036 A1 | 6/2010 | Sufi et al. | |
| 2010/0204554 A1 | 8/2010 | Say et al. | |
| 2010/0291591 A1* | 11/2010 | Wick et al. | 435/7.4 |
| 2011/0033869 A1 | 2/2011 | Bertin | |
| 2011/0189705 A1 | 8/2011 | Gao et al. | |
| 2012/0012472 A1 | 1/2012 | Ahrens et al. | |
| 2012/0034638 A1 | 2/2012 | Ahrens et al. | |
| 2012/0156709 A1 | 6/2012 | Bertin et al. | |
| 2012/0181186 A1 | 7/2012 | Bertin et al. | |
| 2012/0199499 A1 | 8/2012 | O'Connor et al. | |
| 2013/0098777 A1 | 4/2013 | Gaustad et al. | |
| 2013/0112572 A1 | 5/2013 | Bertin et al. | |
| 2013/0236909 A1 | 9/2013 | Bertin | |
| 2013/0264220 A1 | 10/2013 | Bertin et al. | |
| 2014/0027309 A1 | 1/2014 | Bao et al. | |
| 2014/0134658 A1 | 5/2014 | Ahrens et al. | |
| 2014/0311922 A1 | 10/2014 | Ahrens et al. | |
| 2014/0322740 A1 | 10/2014 | Ahrens et al. | |
| 2014/0342383 A1 | 11/2014 | Bertin et al. | |
| 2015/0192538 A1 | 7/2015 | Ahrens et al. | |
| 2015/0198552 A9 | 7/2015 | Ahrens et al. | |
| 2015/0323484 A1 | 11/2015 | Bao et al. | |

FOREIGN PATENT DOCUMENTS

| | | |
|---|---|---|
| WO | 93/03379 | 2/1993 |
| WO | 98/57159 A1 | 12/1998 |
| WO | 99/57317 A1 | 11/1999 |
| WO | 00/11474 | 3/2000 |
| WO | 03/019171 | 3/2003 |
| WO | 2008/045799 | 4/2008 |
| WO | 2009/052422 | 4/2009 |
| WO | 2010/142037 | 12/2010 |
| WO | 2011/041586 | 4/2011 |
| WO | 2011/146143 A2 | 11/2011 |
| WO | 2011/150186 A1 | 12/2011 |

OTHER PUBLICATIONS

International Search Report and Written Opinion dated Jan. 31, 2014 for Application No. PCT/US2013/052324.

Anne et al., Optimizing electrode-attached redox-peptide systems for kinetic characterization of protease action on immobilized substrates. Observation of dissimilar behavior of trypsin and thrombin enzymes. Langmuir. Jun. 12, 2012;28(23):8804-13. Epub May 24, 2012.

Garcia et al., Electrochemical DNA base pairs quantification and endonuclease cleavage detection. Biosens Bioelectron. Sep. 15, 2011;27(1):40-5. Epub Jun. 15, 2011.

Sato et al., Reliable ferrocenyloligonucleotide-immobilized electrodes and their application to electrochemical DNase I assay. Anal Chim Acta. Jul. 10, 2009;645(1-2):30-5. Epub May 6, 2009.

Shipovskov et al., Electrochmical sandwich assay for attomole analysis of DNA and RNA from beer spolage bacteria Lactobacillus brevis. Biosens Bioelectron. Aug.-Sep. 2017;37(1):99-106. Epub May 11, 2012.

Bickert, P., et al., "Pentafulvenes: Versatile Synthons in Metallocene Chemistry," Organometallics, May 1984, vol. 3 (5), pp. 654-657.

Farrington, E.J., et al., "Synthesis and reactivity of a ferrocene-derived PCP-pincer ligand," Chem. Commun., Jan. 21, 2002, pp. 308-309.

Gardner, J.W., et al., "Application of conducting polymer technology in microsystems," Sensors and Actuators, Oct. 1995, vol. 51(1), pp. 57-66. (Abstract only).

Heinze, K., et al., "Main Chain Ferrocenyl Amides from 1-Aminoferrocene-1'-carboxylic Acid," Eur. J. Inorg. Chem., Jul. 2004, vol. 2004(14), pp. 2974-2988. (Abstract only).

Heinze, K., et al., "Anion-Induced Motion in a Ferrocene Diamide," Eur. J. Inorg. Chem., Jan. 2005, vol. 2005 (1), pp. 66-71. (Abstract only).

(56) References Cited

OTHER PUBLICATIONS

Holleman-Wiberg, Inorganic Chemistry, Academic Press 34th Ed., at 1620. (Abstract unavailable).
Hunter, T., "Protein kinases and phosphatases: the yin and yang of protein phosphorylation and signaling," Cell,1995, vol. 80(2), pp. 225-236. (Abstract unavailable).
Karin, M., "Signal transduction and gene control," Curr. Opin. Cell Biol., Jun. 1991, vol. 3(3), pp. 467-473. (Abstract only).
Li, et al., Current Medicinal Chemistry, 2001, vol. 8, pp. 121-133. (Abstract unavailable).
Pichon, et al., "A direct meta-lithiation route to 1,3-disubstituted ferrocenes," Chem. Commun., Feb. 10, 2004, pp. 598-599.
Steurer, et al., "Bromide-Mediated ortho-Deprotonation in the Synthesis of Chiral, Nonracemic Ferrocene Derivatives," Organometallics, Jun. 19, 2007, vol. 26, pp. 3850-3859.
Eur. J. Biochem, 1995, vol. 232, pp. 1-6. (Abstract unavailable).
Eur. J. Biochem, 1996, vol. 237, pp. 1-5. (Abstract unavailable).
Eur. J. Biochem, 1997, vol. 250, pp. 1-6. (Abstract unavailable).
Eur. J. Biochem, 1999, vol. 264, pp. 610-650. (Abstract unavailable).
Abel, et al., Comprehensive Organometallic Chemistry II, A Review of the Literature 1982-1994, vol. 7, chapters 7, 8, 10 & 11, Pergamon Press (abstract unavailable).
Bertin, P.A., et al., "Novel redox active bifunctional crosslinkers from unsymmetrical 1,1'-disubstituted ferrocenes," Tetrahedron Lett., Sep. 23, 2009, vol. 50(38), pp. 5409-5412 (abstract only).
Chen, C., et al., "Chemically Modified Electrodes by Nucleophilic Substitution of Chlorosilylated Platinum Oxide Surfaces," Langmuir, Sep. 1994, vol. 10(9), pp. 3332-3337 (abstract only).
Connelly, et al., "Chemical Redox Agents for Organometallic Chemistry," Chem. Rev., Jan. 9, 1996, vol. 96, pp. 877-910.
Cotton, et al., Advanced Organic Chemistry, 5th Edition, John Wiley & Sons, 1988, p. 38; and chapter 26 (abstract unavailable).
Deinhammer et al., "Electrochemical oxidation of amine-containing compounds: a route to the surface modification of glassy carbon electrodes," Langmuir, 1994, vol. 10(4), pp. 1306-1313 (abstract only).
Gassman, et al., "(Trifluoromethyl)cyclopentadienide: a powerful electron-withdrawing ligand for transition-metal complexes," J. Am. Chem. Soc., Jul. 1986, vol. 108(14), pp. 4228-4229 (abstract only).
Geiger, et al., Advances in Organometallic Chemistry, vol. 23, pp. 1-93 (abstract unavailable).
Geiger, et al., Advances in Organometallic Chemistry, vol. 24, p. 87 (abstract unavailable).
Gray, et al., "Electron Transfer in Proteins," Annual Rev. Biochem, 1996, vol. 65, p. 537-561.
Lenhard, J.R., et al., J. Electroanal. Chem., 1977, vol. 78, pp. 195-201 (abstract unavailable).
Li, et al., "Nanoscale 1,3,5,7-Tetrasubstituted Adamantanes and p-Substituted Tetraphenyl-methanes for AFM Applications," Org. Lett., Sep. 18, 2002, vol. 4(21), pp. 3631-3634 (abstract only).
Lo, L., et al., "Development of highly selective and sensitive probes for hydrogen peroxide," Chem. Commun., 2003, pp. 2728-2729.
Robbins, et al., "Syntheses and electronic structures of decamethylmetallocenes," J. Am. Chem. Soc., Apr. 1982, vol. 104(7), pp. 1882-1893 (abstract only).
Sagi, et al.,"Amperometric Assay for Aldolase Activity; Antibody-Catalyzed Ferrocenylamine Formation," Anal. Chem., 2006, vol. 78(5), pp. 1459-1461 (abstract only).
Sella, E., et al., "Self-immolative dendritic probe for the direct detection of triacetone triperoxide," Chem. Commun., Oct. 15, 2008, Issue 44, pp. 5701-5703 (abstract only).
Wei, et al., "Diverse Redox-Active Molecules Bearing Identical Thiol-Terminated Tripodal Tethers for Studies of Molecular Information Storage," J. Org. Chem., 2004, vol. 69(5), pp. 1461-1469 (abstract only).
Comprehensive Coordination Chemistry, Ed., Wilkinson et al., Pergammon Press, 1987, Chapters 13.2, pp. (73-98), 21.1, pp. (813-898), and 21.3, pp. 915-957 (abstract unavailable).

Xiang, Yu, et al., "Using personal glucose meters and functional DNA sensors to quantify a variety of analytical targets," Nature Chemistry, Sep. 2011, vol. 3, pp. 697-703.
Adjemian, Jocelyne, et al., "Cleavage-Sensing Redox Peptide Monolayers for the Rapid Measurement of the Proteolytic Activity of Trypsin and a-Thrombin Enzymes," Langmuir, Jan. 27, 2010, vol. 26(12), pp. 10347-10356.
Chin, Curtis D., et al, "Microfluidics-Based Diagnostics of Infectious Diseases in the Developing World," Nature Medicine, 2011, vol. 17, pp. 1015-1019, available online Jul. 31, 2011.
Gaster, Richard S., et al., "nanoLAB: An Ultraportable, Handheld Diagnostic Laboratory for Global Health," Lab on a Chip, Dynamic Article Links, Jan. 24, 2011, pp. 1-7.
Houseman, Benjamin T., et al., "Peptide Chips for the Quantitative Evaluation of Protein Kinase Activity," Nature Biotechnology, Research Article, Mar. 2002, vol. 20, pp. 270-274.
Kerman, Kagan, et al., "Electrochemical Detection of Kinase-Catalyzed Thiophosphorylation Using Gold Nanoparticles," Chem. Commun. 2007, pp. 5019-5021.
Kerman, Kagan, et al., "Peptide Biosensors for the Electrochemical Measurement of Protein Kinase Activity," Anal. Chem., 2008, vol. 80, pp. 9395-9401.
Kerman, Kagan, et al., "Electrochemical Detection of Protein Tyrosine Kinase-Catalysed Phosphorylation Using Gold Nanoparticles," Biosensors and Bioelectronics, 2009, vol. 24, pp. 1484-1489.
Kim, S.D., et al., "Gold-Film Array-Electrode for Electrochemical ELISA," Sensors and Actuators B, 2005, pp. 463-469.
Labib, Mahmoud, et al., "A Bioorganometallic Approach for Rapid Electrochemical Analysis of Human Immunodeficiency Virus Type-1 Reverse Transcriptase in Serum," Elsevier, Article in Press, Electrochimica Acta, available online Mar. 22, 2011, pp. 1-7.
Leinonen, J., et al., "Development of Novel Peptide Ligands Modulating the Enzyme Activity of Prostate-Specific Antigen," Scand. J. Clin. Lab. Invest., 2000, pp. 59-64.
Li, Peng, et al., "Development of an Ultrafast Quantitative Heterogeneous Immunoassay on Prefunctionalized Poly (Dimethylsiloxane), Microfluidic Chips for the Next-Generation Immunosensors," Microfluidics and Nanofluidics, vol. 7, No. 4, Mar. 11, 2009.
Martic, Sanela, et al., "Probing the Role of the Linker in Ferrocene-ATP Conjugates: Monitoring Protein Kinase Catalyzed Phosphorylations Electrochemically," Chemistry-A European Journal, 2011, vol. 17, pp. 6744-6752.
Martic, Sanela, et al., "Use of 5-y-Ferrocenyl Adenosine Triphosphate (Fc-ATP) Bioconjugates Having Poly (ethylene glycol) Spacers in Kinase-Catalyzed Phosphorylations," Bioconjugate Chemistry, 2011, pp. 1-10.
Martic, Sanela, et al., "Enzymatically Modified Peptide Surfaces: Towards General Electrochemical Sensor Platform for Protein Kinase Catalyzed Phosphorylations," Analyst, 2011, vol. 136, pp. 107-112.
Nagy, Geza, et al., "Screen-Printed Amperometric Microcell for Proline Iminopeptidase Enzyme Activity Assay," Biosensors & Bioelectronics, 2000, vol. 15, pp. 265-272.
Song, Haifeng, et al., "Electrochemical Detection of Kinase-Catalyzed Phosphorylation Using Ferrocene-Conjugated ATP," Chem. Commun., 2008, pp. 502-504.
Vukmirovic-Popovic, Snezana, et al., "Presence and Enzymatic Activity of Prostate-Specific Antigen in Archival Prostate Cancer Samples," Oncology Reports, 2008, vol. 20, pp. 897-903.
Zhou, Ya-Min, et al., "An Amperometric Immunosensor Based on an Electrochemically Pretreated Carbon-Paraffin Electrode for Complement III (C3) Assay," Biosensors and Bioelectronics, 2008, vol. 18, pp. 473-481.
Batchelor, Robert, et al., "A Resorufin-Based Fluorescent Assay for Quantifying NADH," Analytical Biochemistry, 2002, vol. 305, pp. 118-119.
Beckett, Dorothy, et al., "A Minimal Peptide Substrate in Biotin Holoenzyme Synthetase-Catalyzed Biotinylation," Protein Science, 1999, vol. 8, pp. 921-929.

(56) References Cited

OTHER PUBLICATIONS

Collman, et al., "Role of a Distal Pocket in the Catalytic O2 Reduction by Cytochrome C Oxidase Models Immobilized on Interdigitated Array Electrodes," PNAS, 2009, vol. 106, No. 18, pp. 7320-7323.

Cronan, John E., Jr., "The *E. coli* bio Operon: Transcriptional Repression by an Essential Protein Modification Enzyme," Cell, 1989, vol. 58, pp. 427-429.

Hudson, Richard D.A., "Ferrocene Polymers: Current Architectures, Syntheses and Utility," Journal of Organometallic Chemistry, 2001, pp. 47-69, Abstract only.

Kamidate, Tamio, et al., "Firefly Bioluminescent Assay of ATP in the Presence of ATP Extractant by Using Liposomes," Anal. Chem., 2006, vol. 78, pp. 337-342.

Llaudet, Enrique, et al., "Microelectrode Biosensor for Real-Time Measurement of ATP in Biological Tissue," Anal. Chem., 2005, vol. 77, pp. 3267-3273.

Murphy, Lindy J., et al., "Measurement in Vitro of Human Plasma Glycerol with a Hydrogen Peroxide Detecting Microdialysis Enzyme Electrode," Anal. Chem., 1994, vol. 66, pp. 4345-4353.

Tabata, Masayoshi, et al., "Use of a Biosensor Consisting of an Immobilized NADH Oxidase Column and a Hydrogen Peroxide Electrode for the Determination of Serum Lactate Dehydrogenase Activity," Analytica Chimica Acta, 1994, vol. 298, pp. 113-119.

Wang, Yonghong, et al., "A Sensitive Ligase-Based ATP Electrochemical Assay Using Molecular Beacon-Like DNA," Biosensors and Bioelectronics, 2010, vol. 25, pp. 2101-2106.

Spinke, J., et al., "Molecular Recognition at self-assembled monolayers: Optimization of surface functionalization," The Journal of Chemical Physics, vol. 99, No. 9, Nov. 1993, pp. 7012-7018.

Spinke, J., et al., "Molecular Recognition at self-assembled monolayers: The construction of multicomponent multilayers," Langmuir, 1993, vol. 9(7), pp. 1821-1825.

\* cited by examiner

Figure 2
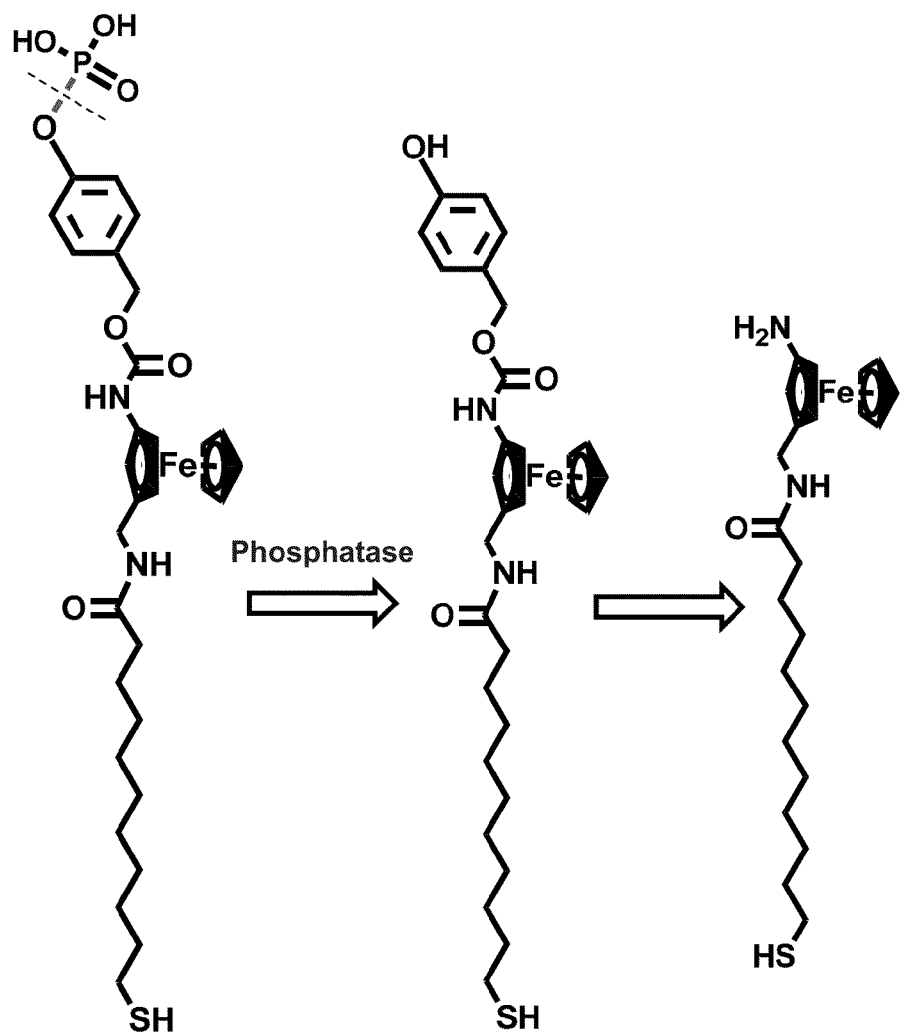
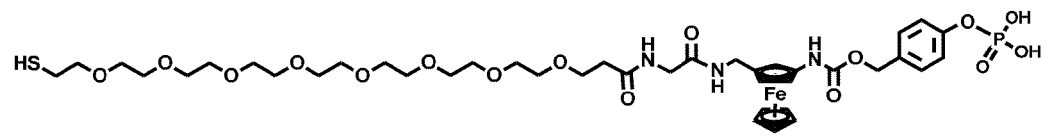

Figure 6
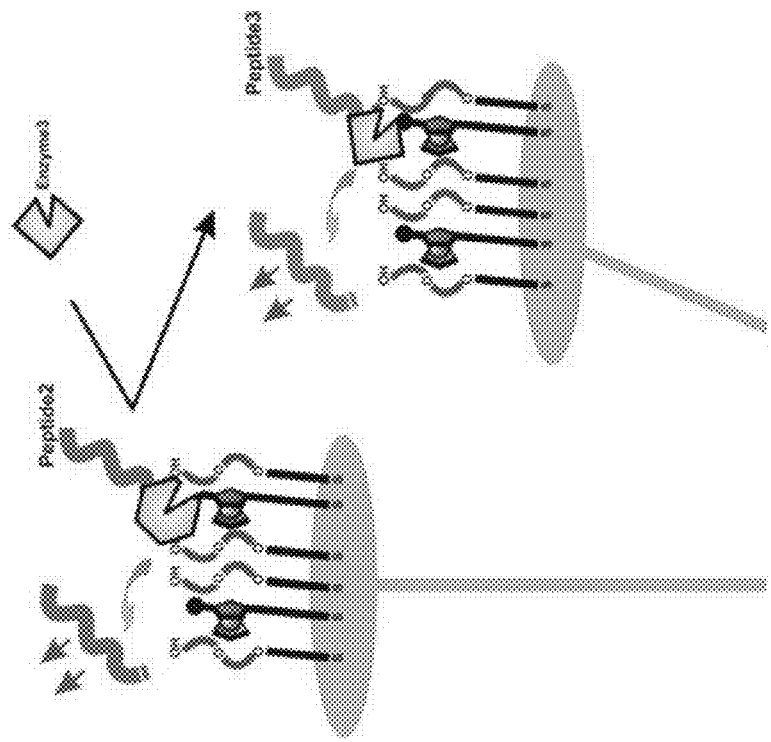
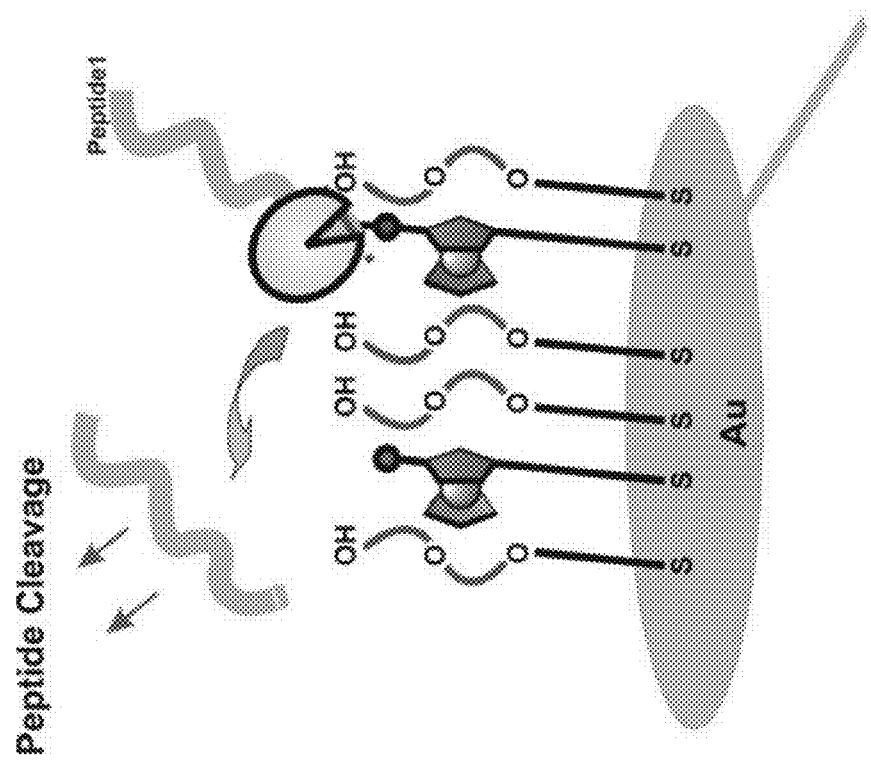

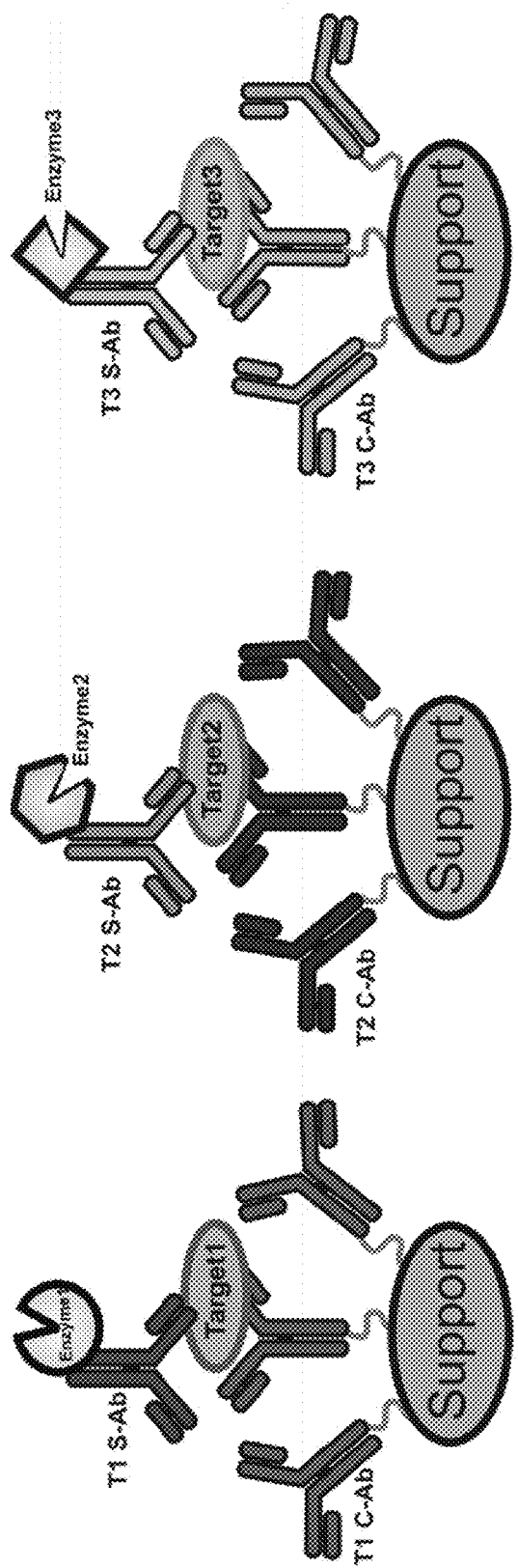

ELECTRIC MEASUREMENT OF MONOLAYERS FOLLOWING PRO-CLEAVE DETECTION OF PRESENCE AND ACTIVITY OF ENZYMES AND OTHER TARGET ANALYTES

CROSS-REFERENCE TO RELATED APPLICATIONS

This application claims the benefit of priority to U.S. Provisional Patent Application No. 61/677,593, filed Jul. 31, 2012, U.S. Provisional Patent Application No. 61/676,641, filed Jul. 27, 2012, and U.S. Provisional Application No. 61/708,301, filed Oct. 1, 2012, the entire disclosures of which are hereby incorporated by reference in their entirety.

FIELD OF THE INVENTION

This invention describes methods for detecting target analytes by utilizing an electroactive moiety (EAM) that functions as a substrate for a specific enzyme. If target analyte (i.e., enzyme) is present, a functional group is enzymatically removed from a transition metal complex resulting in quantifiable electrochemical signal at two unique potentials, $E^0{}_1$ and $E^0{}_2$ that is detected through a self-assembled monolayer (SAM) on an electrode.

BACKGROUND OF THE INVENTION

The electromotive force (EMF) is the maximum potential difference between two electrodes of a galvanic or voltaic cell, where the standard hydrogen electrode is on the left-hand side for the following cell:

| 1 Pt Electrode | $H_2$ | Aqueous Electrolyte Solution | $10^{-3}$M Fe(ClO$_4$)$_3$ $10^{-3}$M Fe(ClO$_4$)$_2$ | 2 Pt |
|---|---|---|---|---|

The EMF is called the electrode potential of the electrode placed on the right-hand side in the graphical scheme of the cell, but only when the liquid junction between the solutions can be neglected or calculated, or if it does not exist at all.

The electrode potential of the electrode on the right-hand side (often called the oxidation-reduction potential) is given by the Nernst equation $$E_{FE^{3+}/FE^{2+}} = E_{FE^{3+}/FE^{2+}}^0 + (RT/F)\ln(a_{FE^{3+}}/a_{FE^{2+}})$$

This relationship follows from equation (2.21) when $(\mu_{FE^{3+}}^0 - \mu_{FE^{2+}}^0)/F$ is set equal to $E_{FE^{3+}/FE^{2+}}^0$ and the pH and ln $p_{H2}$ are equal to zero. In the subscript of the symbol for the electrode potential the symbols for the oxidized and reduced components of the oxidation-reduction system are indicated. With more complex reactions it is particularly recommended to write the whole reaction that takes place in the right-hand half of the cell after symbol E (the 'half-cell' reaction); thus, in the present case $$E_{FE^{3+}/FE^{2+}} = E(Fe^{3+} + E = Fe^{2+})$$

Quantity $E_{Fe^{3+}/Fe^{2+}}^0$ is termed the standard electrode potential. It characterizes the oxidizing or reducing ability of the component of oxidation-reduction systems. With more positive standard electrode potentials, the oxidized form of the system is a stronger oxidant and the reduced form is a weaker reductant. Similarly, with a more negative standard potential, the reduced component of the oxidation-reduction system is a stronger reductant and the oxidized form a weaker oxidant.

The standard electrode $E^0$, in its standard usage in the Nernst equation, equation (1-2) is described as:

$$E = E^0 + \frac{2.3RT}{nF}\log\frac{C_0(0, t)}{C_R(0, t)}$$

where $E^0$ is the standard potential for the redox reaction, R is the universal gas constant (8.314 JK$^{-1}$ mol$^{-1}$), T is the Kelvin temperature, n is the number of electrons transferred in the reaction, and F is the Faraday constant (96,487 coulombs). On the negative side of $E^0$, the oxidized form thus tends to be reduced, and the forward reaction (i.e., reduction) is more favorable. The current resulting from a change in oxidation state of the electroactive species is termed the faradaic.

Previous work describes using conversion of functional groups attached to a transitional metal complex resulting in quantifiable electrochemical signal at two unique potentials, $E^0{}_1$ and $E^0{}_2$. See for example, U.S. Patent Publication Nos. US 2011 0033869 and US 2012-0181186, all herein incorporated by reference in their entirety. The methods generally comprise binding an analyte within a sandwich of binding ligands which may have a functional tag, on a solid support other than the electrode. After target binding, a peroxide generating moiety or an intermediary enzyme and substrate are added which generates hydrogen peroxide. The redox active complex is bound to an electrode and comprises a peroxide sensitive moiety (PSM). The peroxide generated from the enzyme system reacts with the PSM, removing a self-immolative moiety (SIM) and converting functional groups attached to a transitional metal complex resulting in quantifiable electrochemical signal at two unique potentials, $E^0{}_1$ and $E^0{}_2$. This application describes a similar detection scheme however the enzyme target interacts directly with the functional group attached to a transition metal complex, or a functional group attached to a transition metal complex via a self-immolative group resulting in the removal of said groups, altering the functional group substituent of a transitional metal complex resulting in quantifiable electrochemical signal at two unique potentials, $E^0{}_1$ and $E^0{}_2$

SUMMARY OF THE INVENTION

The present invention provides improved composition and methods for the detection of target analytes by introducing an EAM that is a substrate for an enzyme. Unexpectedly, the EAM can be introduced in solution for a homogeneous reaction and subsequently delivered to an electrode for SAM formation or can be immobilized on a pre-formed SAM on an electrode. In particular, the surprising advantages of this system are that the signal transducing molecule, the EAM, also acts as the substrate for enzyme targets, thus eliminating the need for a surrogate target. The elimination of a generic surrogate target enables the detection of multiple enzyme targets (e.g., multiplexed detection) in the same test sample (FIG. 6). Additionally, the compositions and methods of the disclosure are also useful in detection of protein targets through an antibody that is tagged with an appropriate enzyme. Significantly, these methods allow for detection of multiple protein targets in a test sample because each target specific antibody is labeled with a different enzyme and reacts with one of an array of electrodes specifically modified with an EAM designed as a substrate for one and only one of the enzyme tags (FIG. 7).

The targets analytes that could be detected with this invention encompass many different enzyme classes as long as they catalyze the removal a functional group from a precursor molecule, e.g., substrate. Potential enzyme targets include proteases, peptidases, phosphatases, oxidases, hydrolases, lyases, transferases, isomerase, and ligases.

Significantly, this invention also describes methods that allow for truly reagentless detection of target enzymes.

In one aspect, the invention provides compositions and methods for detecting at least one target analyte in a test sample, said method comprising:

(a) contacting a test sample with an electroactive moiety (EAM), said EAM comprising a transition metal complex and an enzyme reactive moiety (ERM) and having a first $E^o$, under conditions wherein said ERM is removed from at least a portion of said EAM provided in the presence of at least one target analyte in the test sample and results in said EAM having a second $E^o$;

(b) detecting for a change between the first $E^o$ and the second $E^o$ of said EAM, wherein said change is an indication of the presence of said at least one target analyte.

In one embodiment of this aspect, provided is a method wherein said at least one target analyte is an enzyme that removes said ERM from said EAM.

In another embodiment of this aspect, provided is a method wherein said at least one target analyte is bound between (i) a capture binding ligand bound to a first solid support and (ii) a soluble binding ligand comprising a surrogate enzyme, said surrogate enzyme is an enzyme that removes said ERM from said EAM.

In one embodiment of the disclosure, any embodiment is where said capture binding ligand and said soluble binding ligand are independently selected from the group consisting of monoclonal antibodies, fragments of monoclonal antibodies, polyclonal antibodies, fragments of polyclonal antibodies, proteins and peptides.

In one aspect, the disclosure provides methods wherein an assay mixture in a solution phase is formed in step (a) and prior to step (b), further comprising step (a1) contacting said assay mixture with a second solid support comprising an electrode or an array of electrodes, under conditions such that a self-assembled monolayer (SAM) forms on said electrode, said EAM having said first $E^o$ and said EAM having said second $E^o$. Thus, in one embodiment of this aspect provided is a method for detecting at least one target analyte in a test sample, said method comprising:

(a) contacting a test sample with an electroactive moiety (EAM) to form an assay mixture in solution phase, said EAM having a first $E^o$ and comprising a transition metal complex and an enzyme reactive moiety (ERM), under conditions wherein said ERM is removed from at least a portion of said EAM provided in the presence of at least one target analyte in the test sample and results in said EAM having a second $E^o$;

(b) contacting said assay mixture with a second solid support comprising an electrode or an array of electrodes under conditions such that a self-assembled monolayer (SAM) forms on said electrode, said EAM having said first $E^o$ and said EAM having said second $E^o$; and (c) detecting for a change between the first $E^o$ and the second $E^o$ of said EAM, wherein said change is an indication of the presence of said at least one target analyte.

In another aspect, the disclosure provides methods wherein said EAM is covalently attached to an electrode or array of electrodes on a second solid support as a self-assembled monolayer (SAM). In one embodiment of this aspect provided is a method for detecting at least one target analyte in a test sample, said method comprising:

(a) contacting a test sample with a second solid support, said solid support comprising an electrode or array of electrodes, said electrode comprising:
  (i) a self-assembled monolayer; and
  (ii) a covalently attached electroactive moiety (EAM), said EAM having a first $E^o$ and comprising a transition metal complex and an enzyme reactive moiety (ERM), under conditions wherein said ERM is removed from at least a portion of said EAM provided in the presence of at least one target analyte in the test sample and results in said EAM having a second $E^o$;

(b) detecting for a change between the first $E^o$ and the second $E^o$ of said EAM, wherein said change is an indication of the presence of said at least one target analyte.

In one embodiment of the disclosure any preceding embodiment where the test sample is further contacted with at least one pro-enzyme under conditions wherein said at least one pro-enzyme is cleaved by said least one target analyte to form at least one surrogate enzyme, said at least one surrogate enzyme removes said ERM.

In one embodiment of the disclosure provided is a method for detecting at least one target analyte in a test sample, said method comprising:

(a) contacting a test sample with at least one pro-enzyme under conditions wherein said at least one pro-enzyme is cleaved by at least one target analyte to form at least one surrogate enzyme;

(b) contacting the surrogate enzyme with an electroactive moiety (EAM) to form an assay mixture in solution phase, said EAM having a first $E^o$ and comprising a transition metal complex and an enzyme reactive moiety (ERM), under conditions wherein said ERM is removed from at least a portion of said EAM provided in the presence of at least one surrogate enzyme in the test sample and results in said EAM having a second $E^o$;

(c) contacting said assay mixture with a solid support comprising an electrode or an array of electrodes under conditions such that a self-assembled monolayer (SAM) forms on said electrode, said SAM comprising said EAM having said first $E^o$ and said EAM having said second $E^o$; and (d) detecting for a change between the first $E^o$ and the second $E^o$ of said EAM, wherein said change is an indication of the presence of said at least one target analyte.

In another embodiment of the disclosure provided is a method for detecting at least one target analyte in a test sample, said method comprising:

(a) contacting a test sample with at least one pro-enzyme under conditions wherein said at least one pro-enzyme is cleaved by at least one target analyte to form at least one surrogate enzyme;

(b) contacting the surrogate enzyme with a solid support, said solid support comprising an electrode or array of electrodes, said electrode comprising:
  (i) a self-assembled monolayer; and
  (ii) a covalently attached electroactive moiety (EAM), said EAM having a first $E^o$ and comprising a transition metal complex and an enzyme reactive moiety (ERM), under conditions wherein said ERM is removed from at least a portion of said EAM provided in the presence of at least one surrogate enzyme in the test sample and results in said EAM having a second $E^o$;

(c) detecting for a change between the first $E^o$ and the second $E^o$ of said EAM, wherein said change is an indication of the presence of said at least one target analyte.

One embodiment of the disclosure provides a method detecting at least one target analyte in a test sample, said method comprising:

(a) contacting a test sample with a capture binding ligand bound to a first solid support under conditions so as to form a first complex in the presence of at least one target analyte;

(b) contacting the first complex with a soluble binding ligand comprising a surrogate enzyme under conditions so as to form a second complex on said first solid support, (c) contacting the second complex with an electroactive moiety (EAM), said EAM comprising a transition metal complex and an enzyme reactive moiety (ERM) and having a first $E^o$, under conditions wherein said ERM is removed from at least a portion of said EAM provided in the presence of at least one target analyte in the test sample and results in said EAM having a second $E^o$; and (d) detecting for a change between the first $E^o$ and the second $E^o$ of said EAM, wherein said change is an indication of the presence of said at least one target analyte, wherein said surrogate enzyme is an enzyme that removes said ERM from said EAM.

In one embodiment a wash step is included between steps (a) and (b).

In another embodiment according to any preceding embodiment, a wash step is included between steps (b) and (c).

In another embodiment according to any preceding embodiment, an assay mixture in a solution phase is formed in step (c) and further comprising step (c1) contacting said assay mixture with a second solid support comprising an electrode or an array of electrodes, under conditions such that a self-assembled monolayer (SAM) forms on said electrode, said EAM having said first $E^o$ and said EAM having said second $E^o$.

In yet another embodiment according to any preceding embodiment, said EAM is covalently attached to an electrode or array of electrodes on a second solid support as a self-assembled monolayer (SAM).

In one embodiment of the disclosure any preceding embodiment where said EAM further comprising a self-immolative moiety (SIM) which joins said ERM to said transition metal complex.

In one embodiment of the disclosure any preceding embodiment where said enzyme reactive moiety (ERM) is selected from the group consisting of an amino acid, peptide, acetate, lipid, carbohydrate, phosphate, or other functional group.

In one embodiment of the disclosure any preceding embodiment where said at least one target analyte is selected from the group consisting of proteases, peptidases, phosphatases, oxidases, hydrolases, lyases, transferases, isomerase, ligases, and ligases or other enzyme that removes a functional group from a substrate or co-substrate.

In one embodiment of the disclosure any preceding embodiment where said surrogate enzyme is selected from the group consisting of proteases, peptidases, phosphatases, oxidases, hydrolases, lyases, transferases, isomerase, ligases, and other enzyme that removes a functional group from a substrate or co-substrate.

In one embodiment of the disclosure any preceding embodiment where said target analyte is Prostate Specific Antigen (PSA).

In one embodiment of the disclosure any preceding embodiment where said transition metal complex includes a transition metal selected from the group consisting of iron, ruthenium and osmium.

In one embodiment of the disclosure any preceding embodiment where said transition metal complex comprises a ferrocene and substituted ferrocene.

In one embodiment of the disclosure any preceding embodiment where said EAM comprises a flexible oligomer anchor tethering said transition metal complex to said electrode, said flexible anchor being an oligomers with polar or charged functional groups in their main chain or side chains examples including poly acrylic acids, polyethylene glycol (PEG), poly vinyl alcohol, polymethacrylate, poly vinylpyrrolidinone, acrylamide, maleic anhydride, and poly vinylpyridine, allylamine, ethyleneimine, oxazoline, and other hydrophobic oligomers with side chains that limit intermolecular hydrophobic interactions and prevent organization and rigidity.

In one embodiment of the disclosure any preceding embodiment where each electrode in said array of electrodes is modified with a SAM comprising a unique EAM, each EAM comprising a unique ERM for a specific target analyte or said surrogate enzyme such that two or more different target analytes may be detected in said test sample.

Another aspect of the disclosure provides compositions comprising a solid support comprising an electrode comprising:

(i) a self-assembled monolayer (SAM); and (ii) a covalently attached electroactive active moiety (EAM) comprising a transition metal complex and an enzyme reactive moiety (ERM), wherein said EAM has a first $E^o$ when said ERM is present and a second $E^o$ when said ERM is absent.

In one embodiment of the composition of the disclosure, the EAM further comprises a self-immolative moiety (SIM) that joins the ERM to the transition metal complex. In another embodiment, the composition of the disclosure comprises said transition metal that is selected from the group consisting of iron, ruthenium and osmium. In another embodiment, the composition of the disclosure comprises said transition metal complex that is a ferrocene or a substituted ferrocene.

In further embodiments of the composition of the disclosure, said EAM comprises a flexible oligomer anchor tethering said transition metal complex to said electrode, said flexible anchor being an oligomers with polar or charged functional groups in their main chain or side chains examples including poly acrylic acids, polyethylene glycol (PEG), poly vinyl alcohol, polymethacrylate, poly vinylpyrrolidinone, acrylamide, maleic anhydride, and poly vinylpyridine, allylamine, ethyleneimine, oxazoline, and other hydrophobic oligomers with side chains that limit intermolecular hydrophobic interactions and prevent organization and rigidity.

In further embodiments of the composition of the disclosure, said solid support comprises an array of electrodes. In even further embodiments of the composition of the disclosure each electrode in said array of electrodes is modified with a SAM comprising a unique EAM, each EAM comprising a unique ERM for a specific target analyte or said surrogate enzyme such that at two or more different target analytes may be detected in said test sample.

Another aspect of the disclosure provides a kit for detecting at least one target analyte in a test sample, the kit comprising any composition of the disclosure.

BRIEF DESCRIPTION OF THE DRAWINGS

FIG. 2 illustrates example structure of a phosphorylated EAM. This EAM acts as a non-specific substrate for phosphatases. Once the phosphate is removed as show by the dashed line the chemical elimination is triggered and the resulting primary amine functionalize ferrocene is show on the right.

FIG. 6 is a representation of multiplexed enzyme (e.g. protease) detection utilizing electrodes specifically modified with different EAM-substrate molecules.

DETAILED DESCRIPTION OF THE INVENTION

Overview

This invention describes a method for which target enzymes could be detected utilizing an EAM (Electro-active Moiety) with an amino acid, amino acid chain (peptide), phosphate, carbohydrate, lipid, acetate or other functional head group that is enzymatically removed resulting in a quantifiable electrochemical signal.

This invention describes the detection of the presence and activity of enzymes, namely proteases, peptidases, phosphatases, oxidases, hydrolases, lyases or transferases. In the methods of disclosure, the signal is detected based on changes in properties of an Enzyme Reactive Moiety (ERM).

Measuring protease activity using this approach would be without use of reagents and directly detects the presence and activity of enzymes in solution. This approach can be applied for multiple enzyme target analytes using uniquely modified electrodes.

The ERM can be either a functional group that can be recognized directly by target analyte, such as proteases, or a surrogate enzyme, such as proteases.

Proteases.

Detection of protease concentration and activity may be used in numerous applications, from drug development and cell state monitoring to clinical relevance on the sample matrix and target of interest. Many cancer biomarkers fall under the protease classification including MMPs, ADAMs, kallikreins, and PSA. Enzymes associated with proteolytic events are also commonly utilized to evaluate cytotoxicity and cell viability. Many current systems used to detect proteases are dependent on an immunoassay format which involves many steps and often times do not provide any assessment of enzyme activity. The ProCleave assay is a means of measuring the concentration of protease, by activity, in a sample matrix. This system offers advantages over other protease detection methods. One advantage, for example is use of a single sample containing multiple targets, delivered to a single reaction chamber, and simultaneously performing multiple measurements. Another advantage offers detecting proteases with ProCleave without the use of additional reagents including no reagents in sample delivery to electrode, reaction, and signal measurement.

Figure 1:
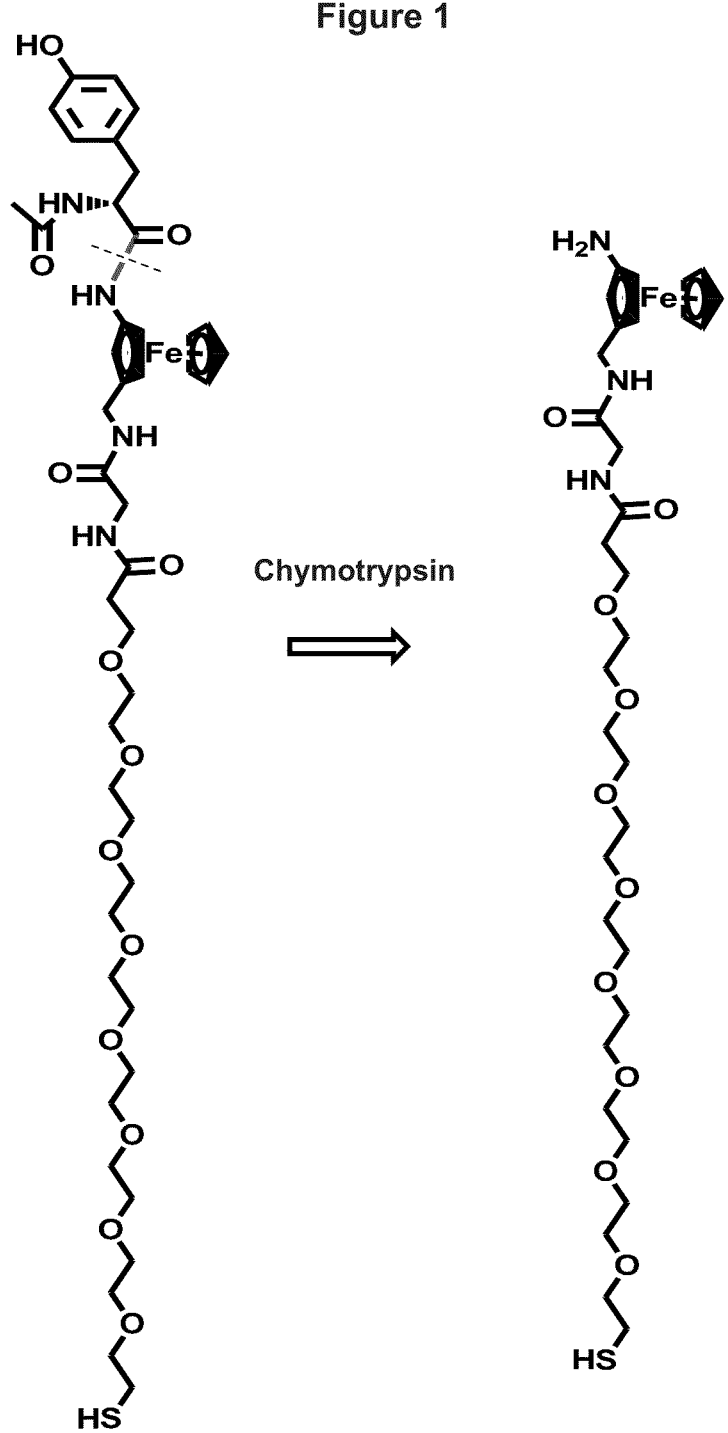
FIG. 1 illustrates example structure of an EAM-substrate molecule where the substrate is a single amino acid, tyrosine. This EAM acts as a substrate for Chymotrypsin which cleaves after tyrosine residues (C-terminus). The cleavage point is show by the dashed line through the highlighted peptide bond. Resulting product is show on the right.
Figure 3:
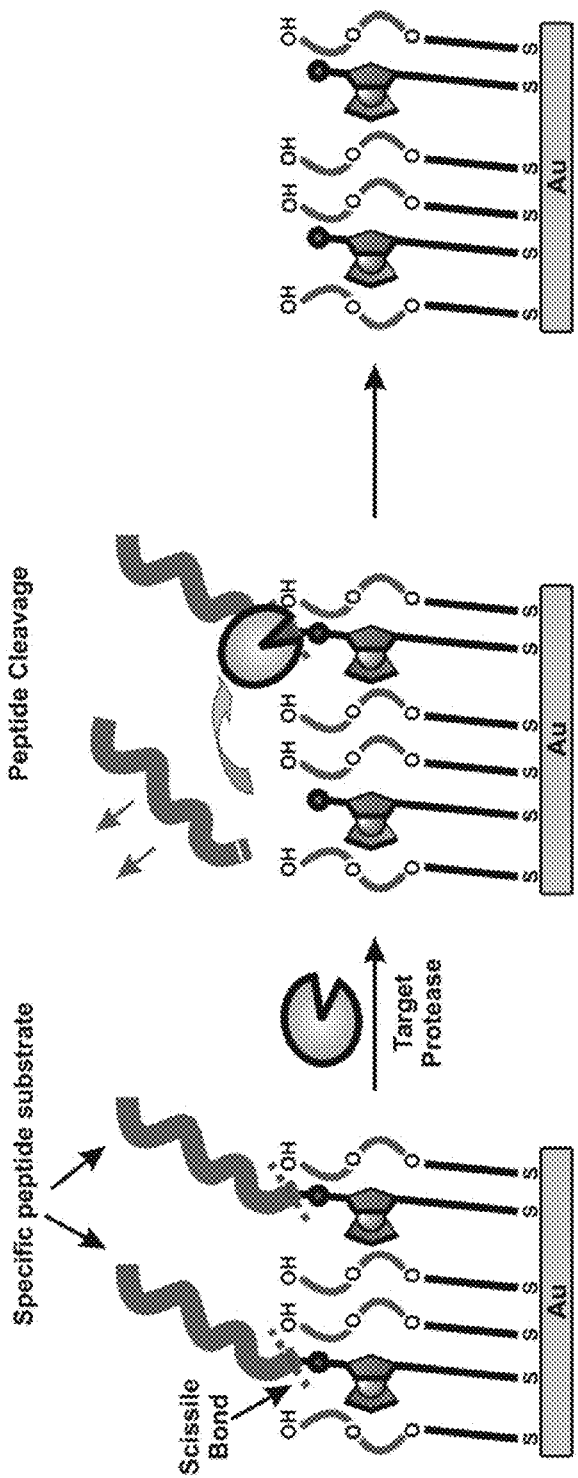
FIG. 3 shows a gold electrode modified with a SAM containing an EAM-Amino acid or EAM-peptide. The peptide on this EAM-peptide molecule acts as a specific substrate for only one protease. The concentration of active target protease in solution is detected through the cleavage of the scissile peptide bond between carboxy terminal residue and the amine head group on the EAM. Cleavage of this amino acid sequence from the EAM results in the appearance of a second redox peak analogous to the $H_2O_2$ based E-TRACE system.

The fundamental element of the ProCleave system is an EAM-peptide (ElectroActive Moiety) molecule that has a dual function as both the enzyme substrate and the electrochemical signal output. The substrate part of the molecule could be a single or multiple amino acid sequence that is chosen to act as a substrate only for the protease of interest. A non limiting example includes, but is not limited to, the detection of PSA activity through the cleavage of an EAM-HSSKLQ substrate. The scissile bond for each peptide substrate is at the C-terminus of the peptide and when cleaved, results in the exposure of the terminal amine of the EAM (FIG. 1). Therefore the substrate specificity is dictated by the amino acids in positions P1-P2-P3; there are no amino acids adjacent to the carboxyl side of the scissile bond in positions P1'-P2'-P3', etc. The substrate is attached to the EAM through a peptide bond such that the initial, intact EAM-peptide exhibits a single formal potential $V_1$. In the presence of the target protease, the substrate is cleaved at the carboxyl-terminus resulting in primary amine-functionalized ferrocene EAM with a negatively shifted apparent formal potential $V_2$, distinct from $V_1$. Therefore the presence of target protease would result in an electrochemical profile with two redox waves, observing a decrease in signal at $V_1$ and an increase of signal at $V_2$ as protease concentration increases. This signal output is analogous to the E-TRACE $H_2O_2$ detection system. In the assay of the disclosure, the signal is produced from an enzymatically catalyzed event not a chemical reaction. This allows for a much more stable initial redox species (EAM) which results in a virtually undetectable background signal level.

Direct Detection Using Phosphatase Tags.

Figure 4:
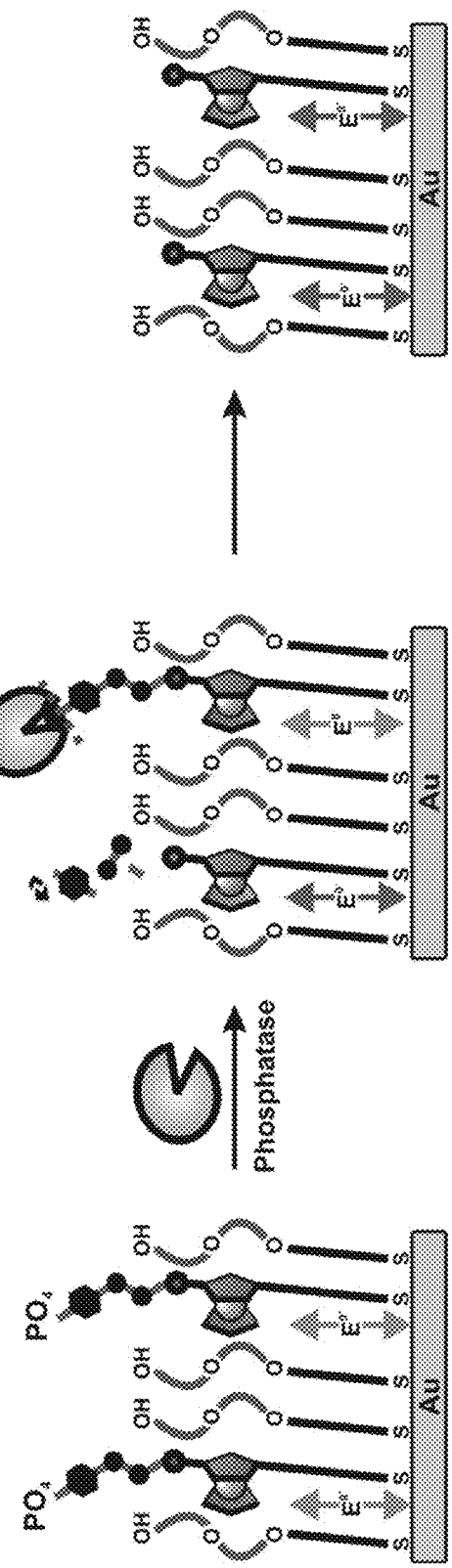
FIG. 4 shows a gold electrode modified with a SAM containing a phosphorylated EAM. The phospho-EAM molecule acts as a substrate for phosphatases in solution. The concentration of active phosphatase in solution is detected through the dephosphorylation of the EAM. This dephosphorylation event triggers a chemical elimination resulting in an exposed primary amine functionalize ferrocene.

Many detection systems rely on enzymatic tags, as surrogate targets or enzymes, to convert a substrate into a detectable signal. A non-limiting example is an Alkaline Phosphatase labeled secondary antibody converting p-Nitrophenyl Phosphate into a colored reaction product detectable via an optical absorbance measurement. The methods of disclosure provide the direct detection of non-specific phosphatases by a specifically designed EAM that acts as a substrate for the phosphatase (FIG. 4). In addition to detecting phosphatases used as surrogate targets, this system may be used to assess the overall phosphatase activity of a sample. Such method may be useful in many applications including cell state monitoring, drug development, and signaling pathway exploration. For many current systems disclosed in the art, this type of measurement would not be possible as the challenges to overcome would be prohibitively complex. For example, current detection techniques utilizing an immunoassay format would be required to detect multiple targets, accurate optical readings in a complex sample matrix would be challenging, and current small molecule based detections would face contamination from native substrate, inhibitors, and scavengers.

The essential component of this application is an EAM molecule that has a dual function as both the enzyme substrate and the electrochemical signal transducer. The substrate moiety in this case is a phosphate group instead of a peptide (FIG. 2). The phenylphosphate head group of EAM exhibits connectivity to the ferrocene such that the initial, intact phosphorylated EAM exhibits a single formal potential $V_1$. In the presence of a phosphatase, the phosphate group is removed resulting in a phenol that undergoes irreversible 1,6-elimination and decarboxylation reactions that will yield a primary amine-functionalized ferrocene EAM with a negatively shifted apparent formal potential, $V_2$. Therefore the presence of target phosphatase would result in an electrochemical profile with two redox waves, observing a decrease in signal at $V_1$ and an increase of signal at $V_2$ as phosphatase concentration increases.

In a surface detection format the structure of the EAM-substrate molecule is central to the success of the assay because it is necessary for the substrate to be accessible to the active site of the protease. A well-ordered semi-crystalline, rigid SAM is not necessarily ideal for this assay given the small size of the substrate and its proximity to a close-packed hydrophobic SAM environment. It is possible that under those conditions the substrate, though exposed on the solution/SAM interface, would yet remain inaccessible to the enzyme active site. Because the ProCleave assay mechanism is a direct change in the chemistry of the EAM and not reliant upon changes in the surrounding environment, the function of the "monolayer" in this assay is to prevent the fouling of the electrode and to tether the EAM-substrate to an addressable electrode. With these considerations in mind, in one embodiment, an EAM-substrate molecule comprises a longer, flexible, hydrophilic anchor (e.g. polyethylene glycol as seen in FIGS. 1 and 2b). Such EAM-substrate molecule is better suited to creating an environment an enzyme can easily diffuse into. Additionally, added flexibility is likely to increase substrate (EAM) accessibility to the enzyme active site.

Another advantage of this particular assay in a surface detection format is the ability to detect many target proteases in one sample simultaneously.

Detection of Proteins Using Enzyme Tagged Antibodies.

Figure 7:
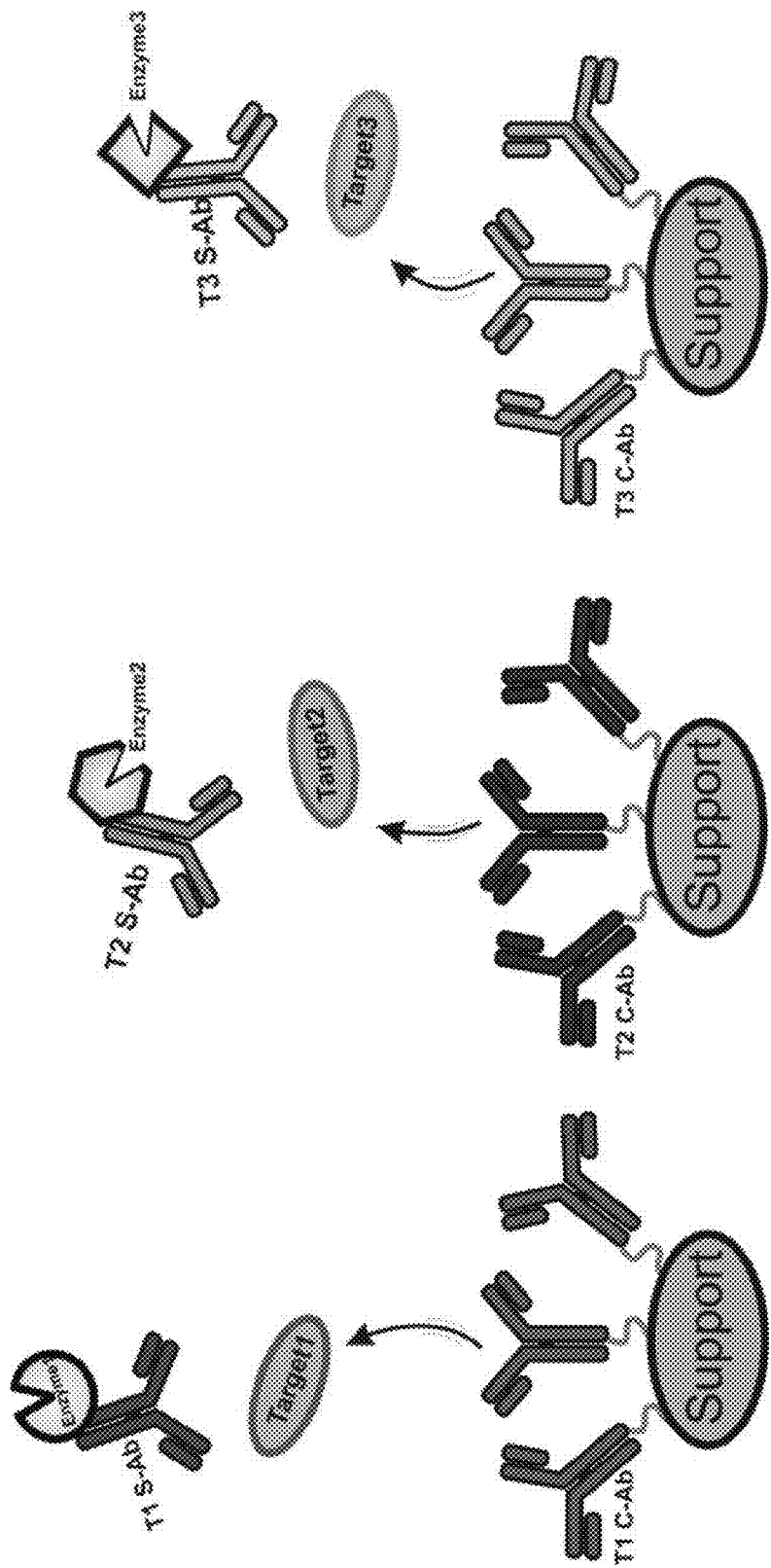
FIG. 7a illustrates protein detection with the ProCleave assay begins by forming an immunosandwich complex for each target like a typical ELISA assay. Solid support (e.g. mix of beads each with capture Abs for different target) is used to form sandwich complexes for each target. Each secondary antibody is has unique enzyme tag.
FIG. 7b illustrates disassociation of the sandwich complex releasing the target/secondary antibody back into solution after residual sample has been washed away using a low pH wash or other methods.
FIG. 7c shows the solution delivered to electrodes. Each electrode is modified with a SAM of unique EAM-amino acid/peptide that serves as a substrate for a specific protease enzyme. The secondary antibody protease tags, acting as surrogate targets, cleave the specific peptide from EAMs on one designated electrode.
Figure 7C:
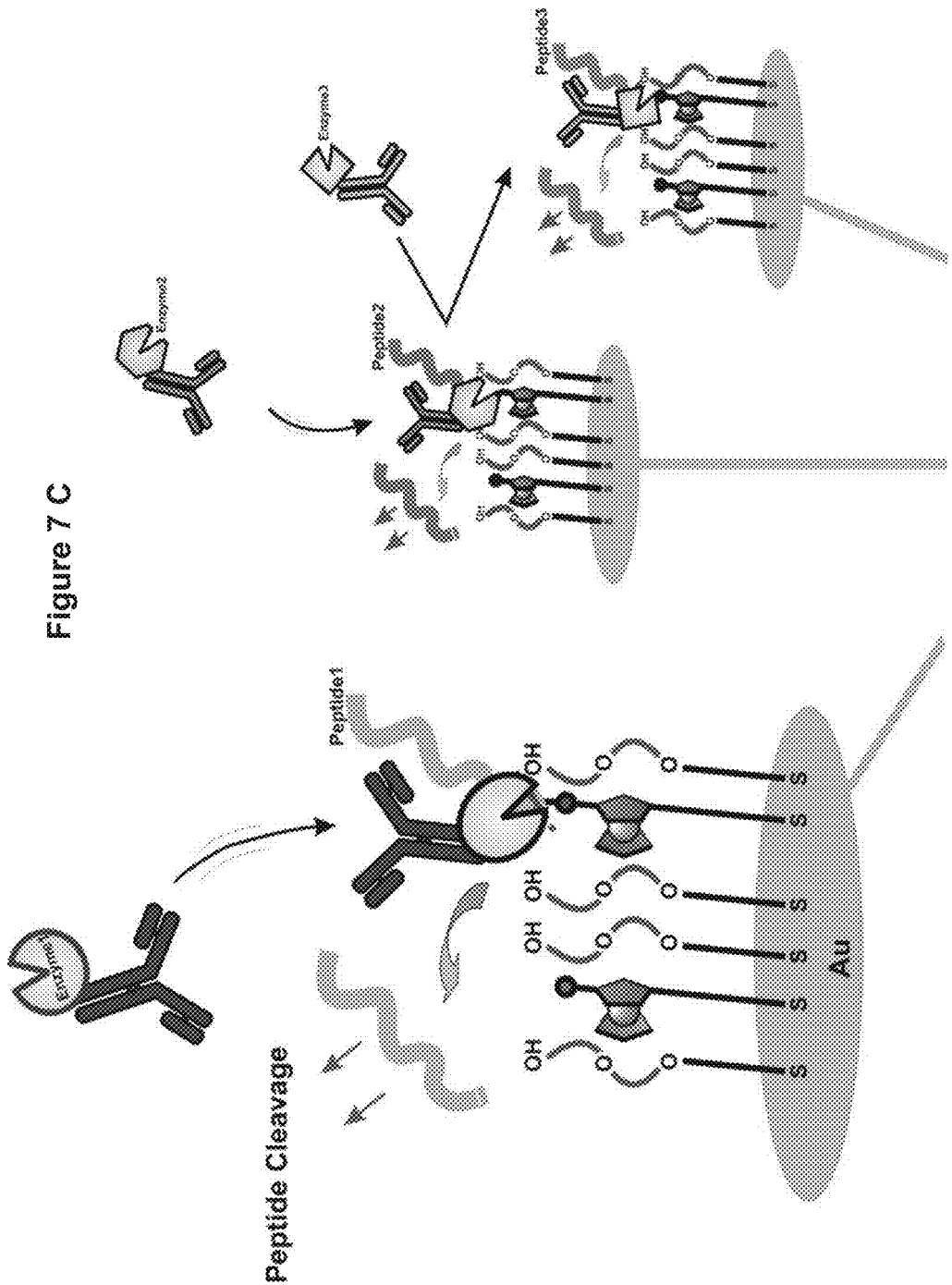
Figure 8:
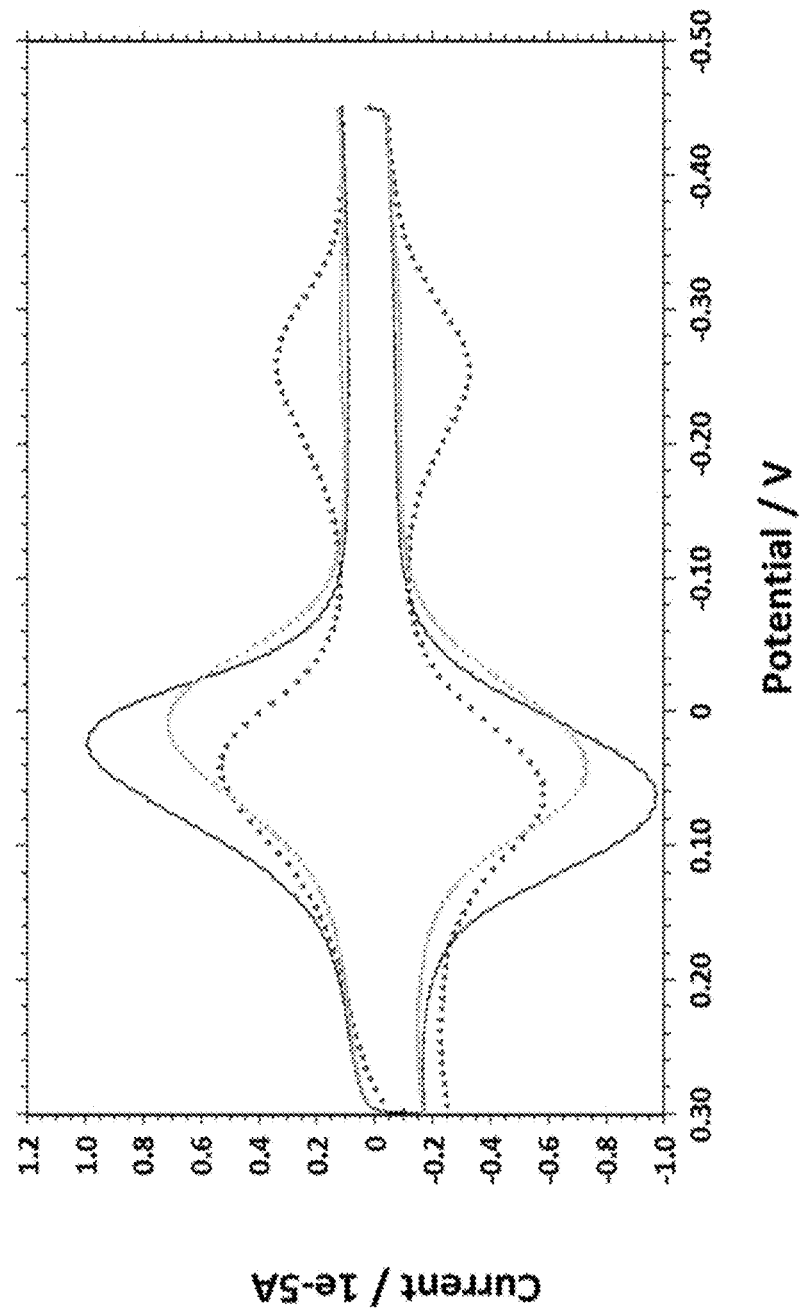
FIG. 8 shows cyclic voltammograms of electrodes incubated for 15 minutes with PBS, 480 nM and 2.4 µM Chymotrypsin (Solid, Dashed, Triangles). A clear positive signal can be observed for 2.4 µM chymotrypsin by the redox wave present at −0.25V and reduced current at 0.06V. A small signal is observed from 480 nM chymotrypsin above baseline as well.
Figure 9:
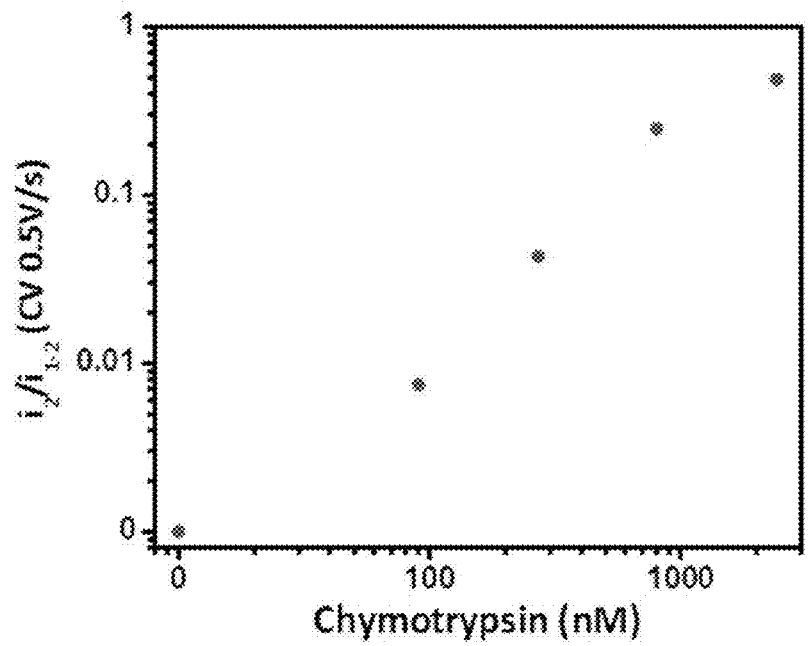
FIG. 9 shows dose response of chymotrypsin incubated with EAM-substrate molecule in a solution phase. Reaction occurs prior to EAM being delivered to electrode for detection.

Another aspect of this invention describes an alternate means of performing the "electrochemical ELISA" where an enzyme tagged secondary antibody serves as a surrogate target rather than a small molecule surrogate target ($H_2O_2$) utilized in Ohmx's E-TRACE assay. The advantage of an enzyme surrogate target is that it provides specificity allowing for detection of multiple targets in the same sample. This detection of multiple targets cannot be accomplished with a generic small molecule surrogate target as signal from one target would be indistinguishable from another. In addition, the detection of multiple targets is a valuable tool in enzyme and protein detection and it presents significant challenge for the current assay systems to provide that capacity. The assay of the disclosure provides the ability to detect multiple proteins, enzymes, or a combination of proteins and enzymes from a single sample in a single well as shown in FIGS. 6 and 7.

Target Analytes

By "target analyte" or "analyte" or "target" or grammatical equivalents herein is meant any molecule, compound or particle to be detected. Target analytes bind to binding ligands (both capture and soluble binding ligands), as is more fully described below or act enzymatically on the EAM itself.

Target Enzymes

In one aspect, the present invention provides methods and compositions useful in the detection of target enzymes. By "analyte", "target analyte" or "target enzyme" herein is meant an enzyme to be detected, including, but not limited to, oxidoreductases, hydrolases (particularly proteases), lyases, isomerases, transferases and ligases. See *Enzyme Nomenclature* 1992, Academic Press, San Diego, Calif., with Supplement 1 (1993), Supplement 2 (1994), Supplement 3 (1995), Supplement 4 (1997) and Supplement 5 (in *Eur. J. Biochem.* 1994, 223, 1-5; *Eur. J. Biochem.* 1995, 232, 1-6; *Eur. J. Biochem.* 1996, 237, 1-5; *Eur. J. Biochem.* 1997, 250; 1-6, and *Eur. J. Biochem.* 1999, 264, 610-650; respectively), herein all incorporated by reference in their entirety. In another aspect, surrogate enzyme may be detected. By "surrogate enzyme" or "surrogate target" herein is meant—an enzyme that that functions as the signal generating part of that detection scheme removing the ERM from the EAM instead of the target analyte itself. This surrogate enzyme is typically tagged onto a capture binding ligand but could also be an inactive enzyme added as a reagent that is activated by the target analyte and once active reacts with EAM removing the ERM and generating signal Hydrolases In some embodiments, the target enzyme is a hydrolase. By "hydrolase" herein is meant an enzyme that catalyzes the hydrolysis of various chemical bonds. They are classified as EC 3 in the EC number classification. Hydrolases include, but are not limited to, enzymes that catalyze ester bonds (esterases, such as nucleases, phophodiesterases, lipases and phosphatases), sugars (carbohydrases including glycosylase/DNA glycosylase, glucoside hydrolase, cellulases, endoglucanases, etc.), ether bonds, peptide bonds (proteases/peptidases), carbon-nitrogen bonds (other than peptide bonds), acid anhydrides (acid anhyride hydrolase, including helicase and GTPase), carbon-carbon bonds, halide bonds, phosphorus-nitrogen bonds, sulfur-nitrogen bonds, carbon-phosphorus bonds, sulfur-sulfur bonds, and carbon-sulfur bonds.

In some embodiments, the hydrolase is a protease (EC 3.4). By "protease" or "proteinase" herein is meant an enzyme that can hydrolyze proteins by hydrolysis of the peptide (amide) bonds that link amino acids. Specifically included within the definition of protease is a peptidase, which specifically refers to an enzyme that hydrolyzes a peptide.

By "proteins" or grammatical equivalents herein is meant proteins, polypeptides, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L configuration. As discussed below, when the protein is used as a capture substrate it may be desirable to utilize protein analogs to retard degradation by sample contaminants, In general, however, if protein analogues are used as the enzyme substrate, the substrate is still able to be processed by the target enzyme.

Proteases are classified into six groups: serine proteases, threonine proteases, cysteine proteases, aspartic acid proteases, metalloproteases, and glutamic acid proteases. In general, protease can either break specific peptide bonds (e.g. specific segments for limited proteolysis), depending on the amino acid sequence of a protein, or break down a complete protein to amino acids (unlimited proteolysis). The activity can be a destructive change, abolishing a protein's function or digesting it to its principal components; it can be an activation of a function, or it can be a signal in a signaling pathway.

In some embodiments, the target enzyme is an endopeptidase. By "endopeptidase" herein is meant peptidases that break peptide bonds within a protein substrate, in contrast to exopeptidases, which break peptide bonds from one or both termini of the protein substrate. Endopeptidases are divided into subclasses on the basis of catalytic mechanism: the serine endopeptidases, cysteine endopeptidases, aspartic endopeptidases, metalloendopeptidases, and other endopeptidases.

A particular protease of interest is PSA (Prostate Specific Antigen). In some embodiments PSA activity can be detected, as a means of differentiating between cancer and benign disease (e.g. Benign prostate hyperplasia). Determining the proteolytic PSA activity in a sample e.g., urine, semen, prostatic fluid or post prostatic massage urine can be correlated to the presence of prostate cancer. This is further described in International patent application No. PCT/US11/00919 (published as WO 2011/146143 and incorporated by reference in its entirety.) PSA can be detected using the methodology described therein by introducing a test sample to an EAM with a specific peptide substrate for PSA (e.g. HSSKLQ-EAM having a first $E^0$) where, if active PSA is present, the Q-EAM bond is cleaved, releasing the peptide and producing and EAM with a second $E^0$ indicating the presence of active PSA.

(1). Serine Endopeptidases

This class comprises two distinct families. The chymotrypsin family which includes the mammalian enzymes such as chymotrypsin, trypsin or elastase or kallikrein and the substilisin family which include the bacterial enzymes such as subtilisin. The general three dimensional (3D) structure is different in the two families but they have the same active site geometry and the catalysis proceeds via the same mechanism. The serine endopeptidases exhibit different substrate specificities which are related to amino acid substitutions in the various enzyme subsites interacting with the substrate residues. Some enzymes have an extended interaction site with the substrate whereas others have a specificity restricted to the P1 substrate residue.

(2). Cysteine Endopeptidases

This family includes the plant proteases such as papain, actinidin or bromelain, several mammalian cathepsins, including lysosomal cathepsins and cathepsin B, L, S, H, J, N and O; the cytosolic calpains (calcium-activated) as well as several parasitic proteases (e.g., *Trypanosoma, Schistosoma*) and caspases, including interleukin converting enzyme (ICE).

(3). Aspartic Endopeptidases

Most of aspartic endopeptidases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral endopeptidases such as the protease from the AIDS virus (HIV) also called retropepsin.

In contrast to serine and cysteine proteases, catalysis by aspartic endopeptidases do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage.

(4). Metallo Endopeptidases

The metallo endopeptidases are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Of particular interest are metalloenzymes including adenosine deaminase, angiotensin converting enzyme, calcineurin, metallo-beta-lactamase, PDE3, PDE4, PDE5, renal dipeptidase, and urease.

In one embodiment, the metallo endopeptidase is a matrix metalloproteinase, including MMP-1 through MMP-10, particularly MMP-1, MMP-2, MMP-7 and MMP-9.

Transferases

In some embodiments, the target enzyme is a transferase. By "transferase" herein is meant an enzyme that catalyzes the transfer of a functional group (e.g. a methyl or phosphate group) from one molecule (the donor) to another (the acceptor).

Transferases are classified as EC 2 in the EC number classification. Transferases can be further classified into nine subclasses: enzymes that transfer one-carbon groups (methyltransferase), enzymes that transfer aldehyde or ketone groups, acyltransferases, glycosyltransferases, enzymes that transfer alkyl or aryl groups, other than methyl groups, enzymes that transfer nitrogenous groups (transaminase), enzymes that transfer phosphorus-containing groups (phosphotransferase, including polymerase and kinase), enzymes that transfer sulfur-containing groups (sulfurtransferase and sulfotransferase), and enzymes that transfer selenium-containing groups.

Eukaryotes employ phosphorylation and dephosphorylation of specific proteins to regulate many cellular processes. T. Hunter, Cell 80:225-236 (1995); Karin, M., Curr. Opin.

Cell Biol. 3:467-473 (1991). These processes include signal transduction, cell division, and initiation of gene transcription. Thus, significant events in an organism's maintenance, adaptation, and susceptibility to disease are controlled by protein phosphorylation and dephosphorylation. These phenomena are so extensive that it has been estimated that humans have around 2,000 protein kinase genes and 1,000 protein phosphatase genes, T. Hunter, Cell 80:225-236 (1995), some of these likely coding for disease susceptibility. For these reasons, protein kinases and phosphatases are good targets for the development of drug therapies.

Oxidoreductases

In some embodiments, the target enzyme is an oxidoreductase. An oxidoreductase is an enzyme that catalyzes the transfer of electrons from one molecule (the oxidant, also called the hydrogen donor or electron donor) to another (the reductant, also called the hydrogen acceptor or electron acceptor). Oxidoreductases are classified as EC 1 in the EC number classification of enzymes. Oxidoreductases can be further classified into 22 subclasses. Many oxidoreductase enzymes are metalloenzymes that contain one or more metal ions. Some examplary enzymes in this group are 4-hydroxyphenylpyruvate dioxygenase, 5-lipoxygenase, alcohol dehydrogenase, aldehyde dehydrogenase, aromatase, cyclooxygenase, cytochrome P450, fumarate reductase, heme oxygenase, lanosterol demethylase, pyruvate:ferredoxin oxidoreductase, ribonucleoside diphosphate reductase, thyroid peroxidase, and xanthine oxidase.

Lyases

In some embodiments, the target enzyme is a lyase. By "lyase" herein is meant an enzyme that catalyzes the breaking of various chemical bonds by means other than hydrolysis and oxidation, often forming a new double bond or a new ring structure.

Lysases are classified as EC 4 in the EC number classification of enzymes. Lyases can be further classified into seven subclasses: (1) lyases that cleave carbon-carbon bonds, such as decarboxylases, aldehyde lyases, and oxo acid lyases; (2) lyases that cleave carbon-oxygen bonds, such as dehydratases; (3) lyases that cleave carbon-nitrogen bonds; (4) lyases that cleave carbon-sulfur bonds; (5) lyases that cleave carbon-halide bonds; (6) lyases that cleave phosphorus-oxygen bonds, such as adenylate cyclase and guanylate cyclase; and (7) other lyases, such as ferrochelatase.

Isomerases

In some embodiments, the target enzyme is an isomerase. By "isomerase" herein is meant an enzyme that catalyses the structural rearrangement of isomers.

Isomerases have their own EC classification of enzymes: EC 5. Isomerases can be further classified into six subclasses: (1) enzymes that catalyze racemization (racemases) and epimerization (epimerases); (2) enzymes that catalyze the isomerization of geometric isomers (cis-trans isomerases); (3) intramolecular oxidoreductases; (4) intramolecular transferases (mutases); (5) intramolecular lyases, and (6) other isomerases (including topoisomerases).

Ligases

Ligases are classified as EC 6 in the EC number classification of enzymes. Ligases can be further classified into six subclasses: (1) enzymes for forming carbon-oxygen bonds (e.g. enzymes acylating a transfer RNA with the corresponding amino acid (amino-acid-tRNA ligases)); (2) enzymes for forming carbon-sulfur bonds (e.g. enzymes synthesizing acyl-CoA derivatives); (3) enzymes for forming carbon-nitrogen bonds (e.g. amide synthases, peptide synthases, enzymes forming heterocyclic rings, enzymes using glutamine as amido-N-donor) and others; (4) enzymes for forming carbon-carbon bonds (the carboxylating enzymes, mostly biotinyl-proteins); (5) enzymes for forming phosphoric ester bonds (e.g. enzymes restoring broken phosphodiester bonds in the nucleic acids (often called repair enzymes)), and (6) enzymes for forming nitrogen-metal bonds (e.g. metal chelation of a tetrapyrrole ring system).

Proenzyme Amplification

Figure 11:
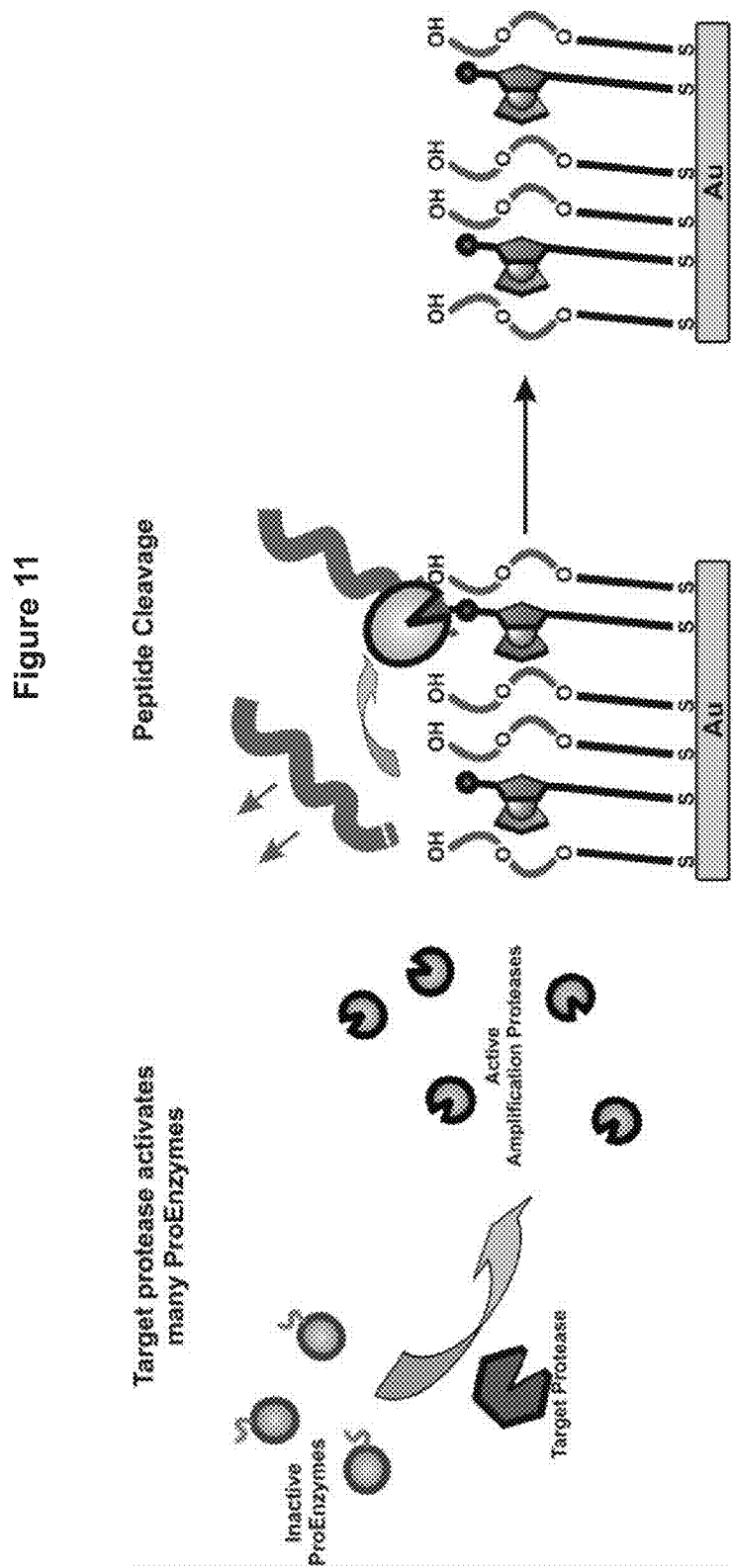
FIG. 11 Illustrates a target protease specifically activating Proenzyme surrogate target supplied in excess. The activated surrogate enzyme reacts with the ERM specific for the surrogate enzyme, removing it from the EAM resulting in a quantifiable signal.

A proenzyme, also known as a zymogen, is an inactive form of an enzyme that becomes active when a propeptide segment is removed. The removal of the prosegment can induce a conformational change or allow access to the previously inaccessible enzyme active site. Since these proenzymes are inactive they can be used as a surrogate target where they are activated by the target of interest "turning on" the proenzyme into its active form which will then react with the ERM of the EAM. Using this proenzyme surrogate target, the signal can be amplified because the proenzyme concentration can be many fold higher than the target analyte. For each target enzyme many proenzymes are activated and react with many more EAMs (FIG. 11). In this case the ERM would act as substrate for the active form of the proenzyme.

Phosphatases

Phosphorylation in biological systems is responsible for regulation across many cell processes including enzyme and receptor activation/deactivation, substrate level phosphorylation in glycolysis and energy storage in oxidative phosphorylation. Post-translational modification, and especially phosphorylation events, is critical to many cell functions including growth, differentiation and metabolism and often times phosphorylation provides a means for signaling pathway deregulation leading to transmogrification in cancer. Phosphorylation is mediated by kinases which phosphorylate and phosphatases which dephosphorylate. This invention provides a method for quantifying the activity of phosphatase, phosphorylation regulators. This could provide a useful tool in many applications including cell state monitoring, drug development, and signaling pathway exploration.

The binding and enzyme reaction conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc. which may be used to facilitate optimal binding and/or reduce non-specific or background interactions. Also reagents that otherwise improve the efficiency of the assay, such as targeted inhibitors, nuclease inhibitors, anti-microbial agents, etc., may be used. The mixture of components may be added in any order that provides for the requisite binding.

The reaction of enzyme with EAM results in the loss of the ERM and/or the ERM-SIM component of the EAM, resulting the a change in the $E^0$ of the EAM. In some embodiments, the $E^0$ of the EAM changes by at about 20 mV, 30 mV, 40 mV, 50 mV, 75 mV, 80 mV, 90 mV to 100 mV, some embodiments resulting in changes of 200, 300 or 500 mV being achieved. In some embodiments, the changes in the $E^0$ of the EAM is a decrease. In some embodiments, the changes in the $E^0$ of the EAM is an increase.

Electron transfer is generally initiated electronically, with voltage being preferred. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used.

Suitable enzyme target analytes incude enyzmes that remove or transfer a functional group from one molecule to another including, proteases, peptidases, phosphatases, oxidases, hydrolases, lyases and transferases, isomerase, and ligases specifically including trypsin, chymotrypsin, PSA, MMPs, ADAMs. Many cancer biomarkers fall under the protease classification including MMPs, ADAMs, kallikreins, and PSA. The proenzyme form of an enzyme belonging to one of those classes can be utilized as a surrogate target to amplify the signal. Enzymes associated with proteolytic events also commonly utilized to evaluate cytotoxicity and cell viability can also be measured with this system.

Other suitable target analytes include therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. that can be immobilized in an antibody or other capture format.

In some embodiments, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g., respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella zoster virus, cytomegalovirus, Epstein Barr virus), rotaviruses, Norwalk viruses, hantavirus, arenavirus, rhabdovirus (e.g. rabies virus), retroviruses (including HIV, HTLV I and II), papovaviruses (e.g. papillomavirus), polyomaviruses, and picornaviruses, and the like), and bacteria (including a wide variety of pathogenic and non-pathogenic prokaryotes of interest including *Bacillus*; *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*; *Staphylococcus*, e.g. *S. aureus*; *Haemophilus*, e.g. *H. influenzae*; *Neisseria*, e.g. *N. meningitidis*, *N. gonorrhoeae*; *Yersinia*, e.g. *G. lamblia Y. pestis*, *Pseudomonas*, e.g. *P. aeruginosa*, *P. putida*; *Chlamydia*, e.g. *C. trachomatis*; *Bordetella*, e.g. *B. pertussis*; *Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone, testosterone; and (4) other proteins (including α-fetoprotein, carcinoembryonic antigen CEA.

In addition, any of the biomolecules for which antibodies may be detected as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

Capture and Soluble Binding Ligands

In addition to SAMs and EAMs, in some embodiments, a solid support comprises capture binding ligands. "Binding ligand" or "binding species" herein is meant a compound that is used to probe for the presence of the target analyte and that will bind to the target analyte. In general, for most of the embodiments described herein, there are at least two binding ligands used per target analyte molecule; a "capture" or "anchor" binding ligand that is attached to a solid support, and a soluble binding ligand, that binds independently to the target analyte, and either directly or indirectly comprises at least one label such as a protease or phosphatase enzyme. By "capture binding ligand" herein is meant a binding ligand that binds the target analyte that is attached to a solid support that binds the target analyte. By "soluble binding ligand" herein is meant a binding ligand that is in solution that binds the target analyte at a different site than the capture binding ligand.

As will be appreciated by those in the art, the composition of the binding ligand will depend on the composition of the target analyte. Binding ligands for a wide variety of analytes are known or can be readily found using known techniques. For example, when the analyte is a protein, the binding ligands include proteins (particularly including antibodies or fragments thereof (FAbs, etc.)) or small molecules.

In general, antibodies are useful as both capture and soluble binding ligands.

The soluble binding ligand also comprises a specific enzyme that is intended to utilize a provided EAM as a substrate. This enzyme tag, also referred to as "surrogate enzyme," could be any enzyme that removes or transfers a functional group from a substrate or co-substrate. It will then specifically remove the respective enzyme reactive moiety (ERM) from the provided EAM.

Generally, the capture binding ligand allows the attachment of a target analyte to the solid support surface, for the purposes of detection. In one embodiment, the binding is specific, and the binding ligand is part of a binding pair. By "specifically bind" herein is meant that the ligand binds the analyte, with specificity sufficient to differentiate between the analyte and other components or contaminants of the test sample. By "specific binding pair" herein is meant a complimentary pair of binding ligands such as an antibody/antigen and receptor/ligand. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-9}$ $M^{-1}$, with at least about $10^{-5}$ to $10^{-9}$ being preferred and at least about $10^{-7}$ to $10^{-9}$ $M^{-1}$ being particularly preferred.

Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Preferred binding ligand proteins include antibodies and peptides. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences.

Samples

The target analytes are generally present in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples, purified samples, raw samples, etc.; as will be appreciated by those in the art, virtually any experimental manipulation may have been done on the sample. Some embodiments utilize target samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage.

Solid Supports

The target analytes are detected using solid supports comprising electrodes. By "substrate" or "solid support" or other grammatical equivalents herein is meant any material that can be modified to contain discrete individual sites appropriate of the attachment or association of capture ligands or EAMs. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with evaporated gold circuits on a polymer backing being particularly preferred. In one embodiment, solid support is selected from microparticles, magnetic microparticles, beads, and microchannels.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer. Accordingly, in a preferred embodiment, the present invention provides chips that comprise substrates comprising a plurality of electrodes, preferably gold electrodes. The number of electrodes is as outlined for arrays. Each electrode becomes modified with a self-assembled monolayer in situ during the last step of the assay as outlined herein. In addition, each electrode has an interconnection, that is the electrode is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety).

Self-Assembled Monolayers

The electrodes comprise either a pre-formed self-assembled monolayer (SAM) or a SAM formed in situ as part of the homogenous assay. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. In addition, a monolayer serves to keep charge carriers away from the surface of the electrode.

In some embodiments the monolayer comprises oligomers, and in particular, oligomers are generally used to attach the EAM to the electrode surface, as described below. In a preferred embodiment the oligomers are flexible and have limited interaction with adjacent molecules such that there is little if any rigidity or organization. Additionally these oligomers may be hydrophilic in order to present a more accessible interface for enzymatic interaction. Due to the disorder and flexibility, these oligomers need not be conductive as the transition metal complex is near enough with sufficient access to the electrode surface as well as the supporting counter ion electrolyte for direct electronic communication through solution to the electrode. Preferred flexible hydrophilic oligomers include oligomers with polar or charged functional groups in their main chain or side chains with these characteristics. Hydrophilic oligomers are also preferred because they increase the solubility of the EAM in aqueous samples. Aqueous samples are ideal for highest enzyme activity therefore EAMs that are more aqueous soluble require less organic solvent to perform the target EAM reaction which in turn will yield higher signal due to increased enzymatic activity. Examples include poly acrylic acids, polyethylene glycol (PEG), poly vinyl alcohol, polymethacrylate, poly vinylpyrrolidinone, acrylamide, maleic anhydride, and poly vinylpyridine. Amine functional oligomers could also be used including allylamine, ethyleneimine, and oxazoline. Other hydrophobic oligomers could be used as well, in particular, oligomers with side chains that limit intermolecular hydrophobic interactions and therefore prevent organization and rigidity. Hydrophobic oligomer linkers could be better suited to particular enzymes as they may have more favorable interactions with hydrophobic regions near enzyme active sites. Ideal oligomer lengths may depend on the target enzyme and monomer structure, with longer oligomers being optimal for enzymatic access but with upper length limitations imposed by electrochemical performance.

In some embodiments, the monolayer comprises conductive oligomers, and in particular, conductive oligomers are generally used to attach the EAM to the electrode surface, as described below. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electro-active polymers, that themselves may donate or accept electrons.

A more detailed description of conductive oligomers is found in WO/1999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

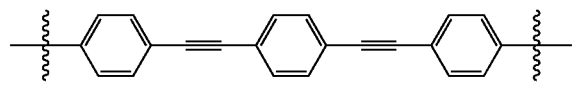

In addition, the terminus of at least some of the conductive oligomers in the monolayer is electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —NH, —OH, —COOH, and alkyl groups such as —CH$_3$, and (poly)alkyloxides such as (poly) ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups.

Thus, for example, some of the terminal groups may facilitate detection, and some may prevent non-specific binding.

The passivation agents thus serve as a physical barrier to block solvent accessibility to the electrode. As such, the passivation agents themselves may in fact be either (1) conducting or (2) nonconducting, i.e. insulating, molecules. Thus, in one embodiment, the passivation agents are conductive oligomers, as described herein, with or without a terminal group to block or decrease the transfer of charge to the electrode. Other passivation agents which may be conductive include oligomers of —$(CF_2)_n$—, —$(CHF)_n$— and —$(CFR)_n$—. In a preferred embodiment, the passivation agents are insulator moieties.

In some embodiments, the monolayers comprise insulators. An "insulator" is a substantially nonconducting oligomer, preferably linear. By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —$(CH_2)_{16}$ molecules, still may transfer electrons, albeit at a slow rate.

In some embodiments, the insulators have a conductivity, S, of about $10^{-7}$ $\Omega^{-1}$ $cm^{-1}$ or lower, with less than about $10^{-8}$ $\Omega^{-1}$ $cm^{-1}$ being preferred. Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer. In some embodiments the insulator comprises $C_6$-$C_{16}$ alkyl.

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the analyte, etc. For example, there may be charged groups on the terminus to form a charged surface to encourage or discourage binding of certain target analytes or to repel or prevent from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them.

The in situ monolayer may comprise a single type of passivation agent, including insulators, or different types.

Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold). In some embodiments, the insulator comprises C6 to C16 alkyl.

In some embodiments, the electrode is a metal surface and need not necessarily have interconnects or the ability to do electrochemistry.

Electroactive Moieties

In addition to the SAMs, the in situ modified electrodes comprise an EAM. By "electroactive moiety (EAM)" or "transition metal complex" or "redox active molecule" or "electron transfer moiety (ETM)" herein is meant a metal-containing compound which is capable of reversibly or semi-reversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention. Metals that find use in the invention also are those that do not change the number of coordination sites upon a change in oxidation state, including ruthenium, osmium, iron, platinium and palladium, with osmium, ruthenium and iron being especially useful. Generally, transition metals are depicted herein (or in incorporated references) as TM or M.

The transitional metal and the coordinating ligands form a metal complex. By "ligand" or "coordinating ligand" (depicted herein or in incorporated references in the figures as "L") herein is meant an atom, ion, molecule, or functional group that generally donates one or more of its electrons through a coordinate covalent bond to, or shares its electrons through a covalent bond with, one or more central atoms or ions.

In some embodiments, small polar ligands are used; suitable small polar ligands, generally depicted herein as "L", fall into two general categories, as is more fully described herein. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Some of the structures of transitional metal complexes are shown below:

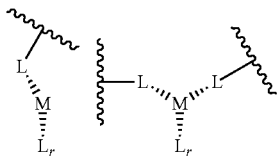

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors, and depicted herein as Lm). Suitable nitrogen donating ligands are well known in the art and include, but are not limited to, cyano (C≡N), $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

As will be appreciated in the art, any ligand donor(1)-bridge-donor(2) where donor (1) binds to the metal and donor (2) is available for interaction with the surrounding medium (solvent, protein, etc) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N=C=O), thiocyanates, isonitrile, $N_2$, $O_2$, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has particular advantages over the others because it is more inert, easier to prepare, more favorable reduction potential. Generally that a larger CN/L ratio will give larger shifts.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In some embodiments, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with .pi.-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [C5H5 (−1)] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [$(C_5H_5)_2$Fe] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example. Other acyclic π-bonded ligands such as the allyl(−1) ion, or butadiene yield potentially suitable organometallic compounds, and all such ligands, in conduction with other .pi.-bonded and .delta.-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

As a general rule, EAM comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, NH2; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocyclic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

In some embodiments, a mixture of monodentate (e.g., at least one cyano ligand), bidentate, tri-dentate, and polydentate ligands can be used in the construction of EAMs.

Of particular use in the present invention are EAMs that are metallocenes, and in particular ferrocenes, which have at least a first self-immolative moiety attached, although in some embodiments, more than one self-immolative moiety is attached as is described below (it should also be noted that other EAMs, as are broadly described herein, with self-immolative moieties can also be used). In some embodiments, when more than one self-immolative moiety is attached to a ferrocene, they are all attached to one of the cyclopentydienyl rings. In some embodiments, the self-immolative moieties are attached to different rings. In some embodiments, it is possible to saturate one or both of the cyclopentydienyl rings with self-immolative moieties, as long as one site is used for attachment to the electrode.

In some embodiments, the EAMs comprise substituted 1,1'-ferrocenes. Ferrocene is air-stable. It can be easily substituted with both capture ligand and anchoring group. Upon binding of the target protein to the capture ligand on the ferrocene which will not only change the environment around the ferrocene, but also prevent the cyclopentadienyl rings from spinning, which will change the energy by approximately 4 kJ/mol. WO/1998/57159; Heinze and Schlenker, Eur. J. Inorg. Chem. 2974-2988 (2004); Heinze and Schlenker, Eur. J. Inorg. Chem. 66-71 (2005); and Holleman-Wiberg, Inorganic Chemistry, Academic Press 34th Ed, at 1620, all incorporated by reference.

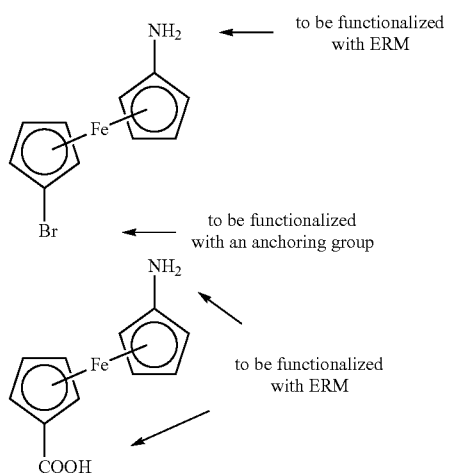

In some other embodiments, the EAMs comprise 1,3-disubstituted ferrocenes. While 1,3-disubstituted ferrocenes are known (see, Bickert et al., *Organometallics* 1984, 3, 654-657; Farrington et al., *Chem. Commun.* 2002, 308-309; Pichon et al., *Chem. Commun.* 2004, 598-599; and Steurer et al., *Organometallics* 2007, 26, 3850-3859), electrochemical studies of this class of molecules in SAMs have not been reported in the literature. In contrast to 1,1'-disubstituted ferrocenes where cyclopentadienyl (Cp) ring rotation can place both Cp substituents in an eclipsed conformation, 1,3-disubstituted ferrocene regioisomers provide a molecular architecture that enforces a rigid geometry between these Cp groups. Representative examples of 1,3-disubstitued ferrocenes are shown below such as compounds 1-5. An example of a 1,3-disubstituted ferrocene for attaching both anchoring and functional ligands is shown below:

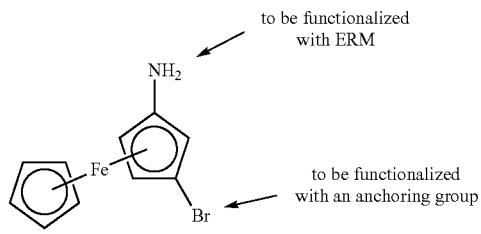

In addition, EAMs generally have an attachment moiety for attachment of the EAM to the conductive oligomer which is used to attach the EAM to the electrode. In general, although not required, in the case of metallocenes such as ferrocenes, the self-immolative moiety(ies) are attached to one of the cyclopentydienyl rings, and the attachment moiety is attached to the other ring, as is generally depicted in FIG. 2, although attachment to the same ring can also be done. As will be appreciated by those in the art, any combination of self-immolative moieties and at least one attachment linker can be used, and on either ring.

In addition to the self-immolative moiety(ies) and the attachment moiety(ies), the ferrocene can comprise additional substituent groups, which can be added for a variety of reasons, including altering the $E^0$ in the presence or absence of at least the self-immolative group. Suitable substituent groups, frequently depicted in associated and incorporated references as "R" groups, are recited in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; and U.S. Provisional Patent Application No. 61/366,013, filed Jul. 20, 2010, hereby incorporated by reference.

In some embodiments, such as depicted below, the EAM does not comprise a self-immolative moiety, in the case where enzyme reactive moiety (ERM) is attached directly to the EAM and provides a change in $E^0$ when the ERM is exposed to a target enzyme. As shown in FIG. 1, one embodiment allows the peroxide-sensitive moiety to be attached directly to the EAM (in this case, a ferrocene), such that the ferrocene has a first $E^0$ when the tyrosine is attached, and a second $E^0$ when removed, e.g., in the presence of chymotrypsin.

Enzyme Reactive Moieties

The substrates being used in the present invention depends on the target enzyme. Enzyme/substrate relationships are generally well known as being characteristics of the relevant target enzyme.

The enzyme reactive moiety (ERM) is an attachment group bound to a substituted transition metal complex such that it fulfills two requirements (1) that it functions as a specific substrate for an enzyme without as limited cross reactivity as possible with other enzymes and (2) that when removed by target or surrogate target enzyme, the direct chemistry change in the EAM or subsequent induced chemical changes (i.e. triggered self-immolative processes) result in the transition metal having a new, distinct $E^0$ from the unreacted starting EAM.

Many suitable ERM groups exist and several are listed below. Therefore, careful consideration must be given to selection and design of ERM and ERM attachment to the transition metal complex. Adjacent groups to the ERM can affect the binding of the ERM in the enzyme active site due to hydrophilic, hydrophobic, steric, hydrogen bonding or van der Waals forces or other interactions resulting in increased or decreased reaction rate. Such attachment considerations include, for instance, amine versus carboxy terminal attachment depending on desired target, peptide length, or inclusion and selection of SIM spacer. In some embodiments a generic substrate (e.g., a phosphate group) is preferred to detect broad activity of phosphatases for example.

Suitable target enzyme/substrate pairs include, but are not limited to, protease/protein, (including protease/peptide), ligase/nucleic acids, ligase/proteins, lipase/lipid, carbohydrase/carbohydrate, kinase/phosphate groups, etc.

For example, when the target enzyme is a protease, the substrate is generally a protein, including peptides, that is cleaved by the target enzyme. In some embodiments, smaller capture substrates are preferred, such as peptides, although larger proteins can be used as well. Again, what is important is that the connectivity of the substituent functional group attached to the transition metal complex is altered as a result of the action of the enzyme changing the electrochemical potential. The substrate preferably also comprises a sequence that can confer specificity to the cleavage, such that each substrate can only be cleaved by one or more specific target enzyme.

Self-Immolative Moieties

The EAMs of the invention include at least one self-immolative moiety that is covalently attached to the EAM such that the EAM has a first $E^0$ when it is present and a second $E^0$ when it has been removed as described below.

The term "self-immolative spacer" or "self-immolative linker" refers to a bifunctional chemical moiety that is capable of covalently linking two chemical moieties into a normally stable tripartate molecule. The self-immolative spacer is capable of spontaneously separating from the second moiety if the bond to the first moiety is cleaved. In the present invention, the self-immolative spacer links an enzyme reactive moiety, e.g., a phosphate group, to the EAM. Upon exposure to a phosphatase enzeym, the phosphate group is removed and the spacer falls apart, as generally depicted in FIG. 2. Generally speaking, any spacer where irreversible repetitive bond rearrangement reactions are initiated by an electron-donating alcohol functional group (i.e. quinone methide motifs) can be designed with boron groups serving as triggering moieties that generate alcohols under oxidative conditions. Alternatively, the boron moiety can mask a latent phenolic oxygen in a ligand that is a pro-chelator for a transition metal. Upon oxidation, the ligand is transformed and initiates EAM formation in the SAM. For example, a sample chelating ligand is salicaldehyde isonicotinoyl hydrazone that binds iron.

As will be appreciated by those in the art, a wide variety of self-immolative moieties may be used with a wide variety of EAMs and peroxide sensitive moieties. Self-immolative linkers have been described in a number of references, including US Publication Nos. 20090041791; 20100145036 and U.S. Pat. Nos. 7,705,045 and 7,223,837, all of which are expressly incorporated by reference in their entirety, particularly for the disclosure of self-immolative spacers.

Figure 10:
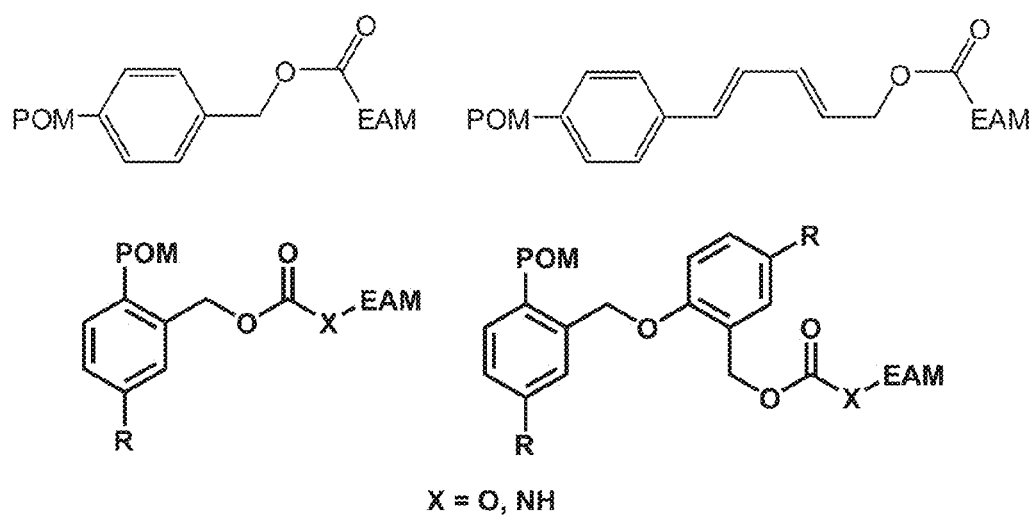
FIG. 10 Illustrates a sample self-immolative spacer groups based on substituted quinone methides.

A few self-immolative linkers of particular use in the present invention are shown in FIG. 10. The self-immolative spacer can comprise a single monomeric unit or polymers, either of the same monomers (homopolymers) or of different monomers (heteropolymers). Alternatively, the self-immolative spacer can be a neighboring group to an EAM in a SAM that changes the environment of the EAM following cleavage analogous to the chemistry as recited in previous application "Electrochemical Assay for the Detection of Enzymes", U.S. Ser. No. 12/253,828, PCT/US2008/080363, hereby incorporated by reference.

Anchor Groups

The present invention provides compounds including the EAM (optionally become attached to the electrode surface with a conductive oligomer), the SAM, that become bound in situ to the electrode surface. Generally, in some embodiments, these moieties are attached to the electrode using anchor group. By "anchor" or "anchor group" herein is meant a chemical group that attaches the compounds of the invention to an electrode.

As will be appreciated by those in the art, the composition of the anchor group will vary depending on the composition of the surface to which it will be attached in situ. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

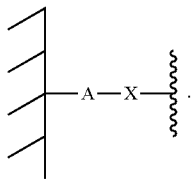

Structure 1

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties.

In some embodiments, the electrode is a carbon electrode, i.e. a glassy carbon electrode, and attachment is via a nitrogen of an amine group. A representative structure is depicted in Structure 15 of US Patent Application Publication No. 20080248592, hereby incorporated by reference in its entirety but particularly for Structures as described therein and the description of different anchor groups and the accompanying text. Again, additional atoms may be present, i.e. linkers and/or terminal groups.

In Structure 16 of US Patent Application Publication No. 20080248592, hereby incorporated by reference as above, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In one preferred embodiment, indium-tin-oxide (ITO) is used as the electrode, and the anchor groups are phosphonate-containing species.

Sulfur Anchor Groups

Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

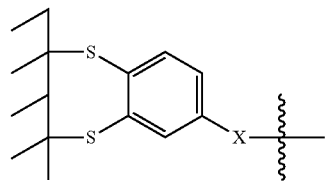

Structure 2

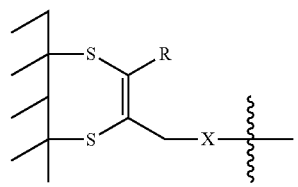

Structure 3

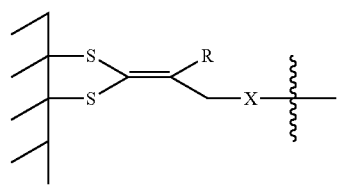

Structure 4

It should also be noted that similar to Structure 4, it may be possible to have a conductive oligomer terminating in a single carbon atom with three sulfur moieties attached to the electrode.

In another aspect, the present invention provides anchors comprising conjugated thiols. In some embodiments, the anchor comprises an alkylthiol group.

In another aspect, the present invention provides conjugated multipodal thio-containing compounds that serve as anchoring groups in the construction of electroactive moieties for analyte detection on electrodes, such as gold electrodes. That is, spacer groups (which can be attached to EAMs, ReAMCs, or an "empty" monolayer forming species) are attached using two or more sulfur atoms. These mulitpodal anchor groups can be linear or cyclic, as described herein.

In some embodiments, the anchor groups are "bipodal", containing two sulfur atoms that will attach to the gold surface, and linear, although in some cases it can be possible to include systems with other multipodalities (e.g. "tripodal"). Such a multipodal anchoring group display increased stability and/or allow a greater footprint for preparing SAMs from thiol-containing anchors with sterically demanding headgroups.

In some embodiments, the anchor comprises cyclic disulfides ("bipod"). Although in some cases it can be possible to include ring system anchor groups with other multipodalities (e.g. "tripodal"). The number of the atoms of the ring can vary, for example from 5 to 10, and also includes multicyclic anchor groups, as discussed below In some embodiments, the anchor groups comprise a [1,2,5]-dithiazepane unit which is seven-membered ring with an apex nitrogen atom and a intramolecular disulfide bond as shown below:

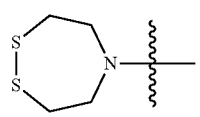

Structure 5

In Structure (5), it should also be noted that the carbon atoms of the ring can additionally be substituted. As will be appreciated by those in the art, other membered rings are also included. In addition, multicyclic ring structures can be used, which can include cyclic heteroalkanes such as the [1,2,5]-dithiazepane shown above substituted with other cyclic alkanes (including cyclic heteroalkanes) or aromatic ring structures.

In some embodiments, the anchor group and part of the spacer has the structure shown below Structure 6

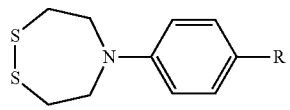

The "R" group herein can be any substitution group, including a conjugated oligophenylethynylene unit with terminal coordinating ligand for the transition metal component of the EAM.

The anchors are synthesized from a bipodal intermediate (I) (the compound as formula III where R=I), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

As will be appreciated by those in the art, the compositions of the invention can be made in a variety of ways, including those outlined below and in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; U.S. Provisional Patent Application No. 61/366,013, filed Jul. 20, 2010. In some embodiments, the composition are made according to methods disclosed in of U.S. Pat. Nos. 6,013,459, 6,248,229, 7,018,523, 7,267,939, U.S. patent application Ser. Nos. 09/096,593 and 60/980,733, and U.S. Provisional Application No. 61/087,102, filed on Aug. 7, 2008, all are herein incorporated in their entireties for all purposes.

Applications

Figure 5:
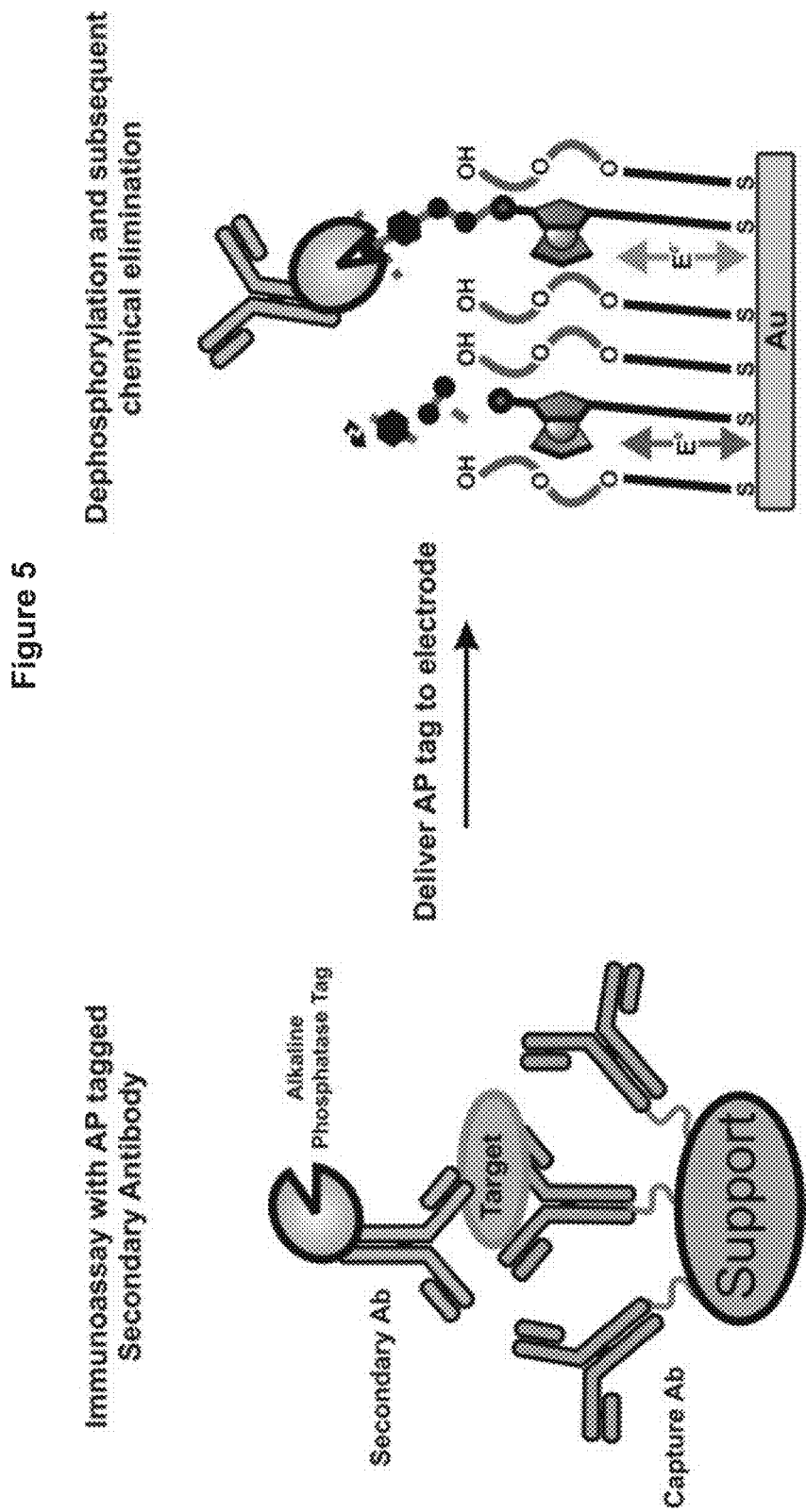
FIG. 5 shows an example protein detection application of this invention. In an immunoassay format Alkaline Phosphatase (AP) is tagged to the secondary antibody. This antibody is delivered to the electrode where AP dephosphorylates the EAM, triggering the release of the self-immolative linker, altering the functional group substituent of a transitional metal complex resulting in quantifiable electrochemical signal at two unique potentials, $E^o_1$ and $E^o_2$ dependent on AP concentration.

The systems of the invention find use in the detection of a variety of target analytes, as outlined herein. In some embodiments, for example, the detection of particular enzymes such as proteases e.g., chymotrypsin, trypsin, PSA, MMPs, phosphatases, lyases, hydrolases and transferases. In other embodiments, "sandwich" type assays are used, as are generally depicted in FIG. 5.

In some embodiments, for example in "sandwich" type formats, the target analyte, contained within a test sample, is added to the solid support comprising a capture binding ligand. This addition is followed by an optional washing step and the addition of the enzyme tagged soluble binding ligand, although as will be appreciated by those in the art, these additions can be done simultaneously or the solution binding ligand can be added to the sample containing the target analyte prior to addition to the solid support. The surface is again optionally washed, and subsequently the target sandwich bound to the solid support is delivered to the EAM. In some embodiments this EAM is in the solution phase and in other embodiments this EAM is immobilized in a pre-formed SAM on an electrode. The enzyme tag on the soluble binding ligand enzymatically reacts with the ERM of the EAM resulting in reacted EAMs exhibiting an electrochemical signal at $E^o{}_2$. The amount of reacted and unreacted EAMs can then be measure by quantifying the electrochemical signal at $E^o{}_2$ and $E^o{}_1$ respectively. In the case where the EAM is in the solution phase, the assay mixture containing reacted and unreacted EAM and the sandwich complex is delivered to an electrode for SAM formation and detection.

In some embodiments after the sandwich complex has been isolated, it may be disassociated such that the enzyme tagged soluble binding ligand is released from the solid support into the solution phase. The solution phase soluble binding ligand is then delivered to the EAM for reaction where in some embodiments this EAM is in the solution phase and in other embodiments this EAM is immobilized in a pre-formed SAM on an electrode.

Detection

Electron transfer between the redox active molecule and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte.

The device for measuring electron transfer amperometrically involves sensitive current detection and includes a means of controlling the voltage potential, usually a potentiostat. This voltage is optimized with reference to the potential of the redox active molecule.

In some embodiments, alternative electron detection modes are utilized. For example, potentiometric (or voltammetric) measurements involve non faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capacitance) could be used to monitor electron transfer between the redox active molecules and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal to noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock in" amplifiers of detection, orders of magnitude improvements in signal to noise may be achieved.

In some embodiments, electron transfer is initiated and detected using direct current (DC) techniques. As noted above, the first $E^0$ of the redox active molecule before and the second $E^0$ of the reacted redox active molecule afterwards will allow the detection of the analyte. As will be appreciated by those in the art, a number of suitable methods may be used to detect the electron transfer.

In some embodiments, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred.

In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages of from about 1 V to about +1.1 V are preferred, with from about 500 mV to about +800 mV being especially preferred, and from about 300 mV to about 500 mV being particularly preferred. On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to the first and second $E^0$ of the redox active molecules, molecules on the basis of the rate of electron transfer, which in turn can be used either to distinguish the two on the basis of frequency or overpotential.

In some embodiments, measurements of the system are taken at least two separate amplitudes or overpotentials, with measurements at a plurality of amplitudes being preferred. As noted above, changes in response as a result of changes in amplitude may form the basis of identification, calibration and quantification of the system.

In some embodiments, the AC frequency is varied. At different frequencies, different molecules respond in different ways. As will be appreciated by those in the art, increasing the frequency generally increases the output current. However, when the frequency is greater than the rate at which electrons may travel between the electrode and the redox active molecules, higher frequencies result in a loss or decrease of output signal. At some point, the frequency will be greater than the rate of electron transfer through even solvent inhibited redox active molecules, and then the output signal will also drop.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In some embodiments, measurements of the system are taken at least two separate frequencies, with measurements at a plurality of frequencies being preferred. A plurality of frequencies includes a scan. In a preferred embodiment, the frequency response is determined at least two, preferably at least about five, and more preferably at least about ten frequencies.

Signal Processing

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

Apparatus

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands.

The apparatus further comprises a voltage source electrically connected to the test chamber; that is, to the measuring electrodes. Preferably, the voltage source is capable of delivering AC and DC voltages, if needed.

In an embodiment, the apparatus further comprises a processor capable of comparing the input signal and the output signal. The processor is coupled to the electrodes and configured to receive an output signal, and thus detect the presence of the target analyte.

EXAMPLES

Example 1

Detection of Chymotrypsin with a Surface Based Reaction

A neat SAM of EAM shown in FIG. 1 was grown at a concentration of 100 μM for 5 hours in ethanol. Electrode was then washed with ethanol followed by water. Lyophilized chymotrypsin was re-suspended in PBS pH 7.4. 40 μL of target solution (PBS, 2.4 μM Chymotrypsin, 480 nM Chymotrypsin) was delivered to separate electrodes and incubated at room temperature for 15 minutes. Target solution was then removed, electrode was rinsed with water, and testing solution was applied. Numerical values demonstrating dose response to chymotrypsin are shown in Table 1 below.

TABLE 1

| Chymotrypsin PBS pH 7.4 concentration | Signal |
| --- | --- |
| 0 nM | 0 |
| 480 nM | 0.031 |
| 2.4 μM | 0.588 |

Example 2

Detection of Chymotrypsin with a Solution Based Homogeneous Reaction

To account for the solution reaction rates being faster than surface reactions, due to both diffusion and enzymatic accessibility limitations, the ProCleave assay was executed using the EAM-substrate molecule as a solution probe. The EAM-substrate was delivered to the sample and allowed to react. After enzymatic cleavage occurred in solution, the sample was delivered to the gold electrode for detection. Reacted/unreacted EAMs from solution became tethered to the electrode and a measurement was performed. This method of detection was utilized because the unique self-calibration of the system's signal output provided a reliable measurement without the formation of an ordered, well-packed SAM.

Titration of alpha human Chymotrypsin was made in PBS pH7.4. 90 μL of this solution was transferred to a new tube. 10 μL of a 1 mM stock (in ethanol) of EAM2 (shown below) was spiked into 90 μL of chymotrypsin titration to yield a final concentration of 100 μM EAM (10% Ethanol) solution. The reaction was performed for 1 hour. Solution was then applied to electrode for a 45 minute SAM formation. Target solution was then removed, electrode was rinsed with water, and testing solution was applied. Numerical values demonstrating dose response for this assay are shown in Table 2 below.

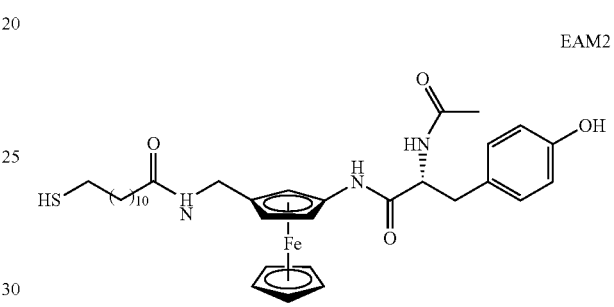

EAM2

TABLE 2

| Chymotrypsin PBS pH 7.4 concentration | Signal |
| --- | --- |
| 0 nM | 0 |
| 90 nM | 0.0075 |
| 267 nM | 0.0433 |
| 800 nM | 0.247 |
| 2.4 μM | 0.487 |

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

We claim:

1. A method for detecting at least one target analyte in a test sample, said method comprising:
    (a) contacting a test sample with an electroactive moiety (EAM), wherein said EAM comprises a transition metal complex and an enzyme reactive moiety (ERM) and has a first E°, and wherein said ERM is removed from at least a portion of said EAM in the presence of at least one target analyte in the test sample and results in said EAM having a second E°;

(b) detecting for a change between the first $E^o$ and the second $E^o$ of said EAM, wherein said change is an indication of the presence of said at least one target analyte, wherein an assay mixture in a solution phase is formed in step (a) and prior to step (b), and further comprising contacting said assay mixture with a solid support comprising an electrode, under conditions such that a self assembled monolayer (SAM) forms on said electrode.

2. The method according to claim 1, wherein said at least one target analyte is an enzyme that removes said ERM from said EAM.

3. The method according to claim 1, wherein said at least one target analyte is bound between (i) a capture binding ligand bound to a second solid support and (ii) a soluble binding ligand comprising a surrogate enzyme, said surrogate enzyme is an enzyme that removes said ERM from said EAM.

4. The method according to claim 3, wherein when the method is to detect two or more test analytes in the test sample, the test sample is contacted with two or more EAMs, each EAM being-unique and comprising a unique ERM for a specific target analyte or surrogate enzyme such that two or more different target analytes are detected in said test sample.

5. The method according to claim 3, wherein said capture binding ligand and said soluble binding ligand each independently comprise a monoclonal antibody, a fragment of a monoclonal antibody, polyclonal antibodies, fragments of polyclonal antibodies, a protein, or a peptide.

6. The method according to claim 1, wherein said EAM further comprises a self-immolative moiety (SIM) which joins said ERM to said transition metal complex.

7. The method according to claim 1, wherein said ERM is an amino acid, peptide, acetate, lipid, carbohydrate, phosphate, or other functional group.

8. The method according to claim 1, wherein said at least one target analyte is a/an protease, peptidase, phosphatase, oxidase, hydrolase, lyase transferase, isomerase, or ligase.

9. The method according to claim 3, wherein said surrogate enzyme is a/an protease, peptidase, phosphatase, oxidase, hydrolase, lyase, transferase, isomerase, or ligase.

10. The method according to claim 1, wherein said target analyte is Prostate Specific Antigen (PSA).

11. The method according to claim 1, wherein said transition metal complex comprises iron, ruthenium, or osmium.

12. The method according claim 1, wherein said transition metal complex comprises ferrocene or substituted ferrocene.

13. The method according claim 1, wherein said EAM comprises a flexible oligomer anchor tethering said transition metal complex to said electrode, said flexible oligomer anchor being an oligomer with polar or charged functional groups in its main chain or side chains.

14. The method according to claim 13, wherein said flexible oligomer anchor comprising poly acrylic acid, polyethylene glycol (PEG), poly vinyl alcohol, polymethacrylate, poly vinyl-pyrrolidinone, acrylamide, maleic anhydride, poly vinylpyridine, allylamine, ethyleneimine, oxazoline, or other hydrophobic oligomer with side chains that limit intermolecular hydrophobic interactions and prevent organization and rigidity.

15. The method according to claim 1, wherein when the method is to detect two or more test analytes in the test sample, the test sample is contacted with two or more EAMs, each EAM being unique and comprising a unique ERM for a specific target analyte such that two or more different target analytes are detected in said test sample.

16. The method according to claim 1, wherein said at least one target analyte is an enzyme that activates a proenzyme, and wherein said proenzyme when activated removes said ERM from said EAM.

17. The method according to claim 1, wherein said at least one target analyte is bound between (i) a capture binding ligand bound to a second solid support and (ii) a soluble binding ligand comprising an enzyme tag, wherein said enzyme tag activates a proenzyme that removes said ERM from said EAM.

18. The method according to claim 1, further comprising one or more wash steps are performed prior to step b.

19. A method for detecting at least one target analyte in a test sample, said method comprising:
(a) contacting a test sample with an electroactive moiety (EAM) to form an assay mixture in solution phase, said EAM having a first $E^o$ and comprising a transition metal complex and an enzyme reactive moiety (ERM), wherein said ERM is removed from at least a portion of said EAM in the presence of at least one target analyte in the test sample and results in said EAM having a second $E^o$;
(b) contacting said assay mixture with a solid support comprising an electrode under conditions such that a self-assembled monolayer (SAM) forms on said electrode, said SAM comprising said EAM having said first $E^o$ and said EAM having said second $E^o$; and
(c) detecting for a change between the first $E^o$ and the second $E^o$ of said EAM, wherein said change is an indication of the presence of said at least one target analyte.

* * * * *